United States Patent [19]
Bergsma et al.

[11] Patent Number: 5,912,335
[45] Date of Patent: Jun. 15, 1999

[54] G-PROTEIN COUPLED RECEPTOR HUVCT36

[75] Inventors: Derk J. Bergsma, Berwyn, Pa.; Catherine E. Ellis, Glassboro, N.J.

[73] Assignee: SmithKline Beecham Corporation, Philadelphia, Pa.

[21] Appl. No.: 08/724,974

[22] Filed: Oct. 3, 1996

[51] Int. Cl.⁶ .......................... C12N 15/12; C07K 14/705
[52] U.S. Cl. .................. 536/23.5; 435/69.1; 435/252.3; 435/320.1; 530/350
[58] Field of Search ................................. 435/69.1, 253.2, 435/325, 320.1; 536/23.5

[56] References Cited

PUBLICATIONS

An, S., Tsai, C., Goetzl, E.J., "Cloning, sequencing and tissue distribution of two related G protein–coupled receptor candidates expressed prominently in human lung tissue", FEBS Letters, 1995, 375:121–125.

An, S., GenBank Submission, Accession No. U35398, "Human G protein–coupled receptor mRNA, complete cds."

Heiber, M., et al., "Isolation of Three Novel Human Genes Encoding G Protein–Coupled Receptors", DNA and Cell Biology, 1995, 14(1):25–35.

Ye, R.D., Prossnitz, E.R., Zou, A. and Cochrane, C.G., "Characterization of a Human cDNA that Encodes a Functional Receptor for Platelet Activating Factor", Biochemical and Biophysical Research Communications, 1991, 180(1):105–111.

Ngo et al. In: The Protein Folding Problem and Tertiary Structure Prediction.1994, Merz et al. (ed.) Birkhauser, Boston, MA pp. 433, 492–495.

Songzhu et al. 1995 FEBS Letters 375: 121–124.

Mahadevan et al. 1995 Genomics 30: 84–88.

Heiber et al. 1995 DNA and Cell Biol. 14:25–35.

George et al. "Current Methods in Sequence Comparison and Analysis". Macromolecular Sequencing and Synthesis, Selected Methods an Applications. pp. 127–149, Jul. 1988.

*Primary Examiner*—John Ulm
*Attorney, Agent, or Firm*—Ratner & Prestia; William T. King; William T. Han

[57] ABSTRACT

Human HUVCT36 polypeptides and DNA (RNA) encoding such HUVCT36 and a procedure for producing such polypeptides by recombinant techniques is disclosed. Also disclosed are methods for utilizing such HUVCT36 for the treatment of infections, such as bacterial, fungal, protozoan and viral infections, particularly infection caused by HIV-1 or HIV-2; pain; cancers; anorexia; bulimia; asthma; Parkinson's disease; acute heart failure; hypotension; hypertension; urinary retention; osteoporosis; angina pectoris; myocardial infarction; ulcers; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's, among others, are also disclosed. Also disclosed are diagnostic assays for detecting diseases related to mutations in the nucleic acid sequences and altered concentrations of the polypeptides. Also disclosed are diagnostic assays for detecting mutations in the polynucleotides encoding the HUVCT36 and for detecting altered levels of the polypeptide in a host.

5 Claims, 3 Drawing Sheets

Nucleotide sequence and Amino Acid sequence of HUVCT36

```
      GAGCTCGAGCGATCCCCACCTCCCAAAGTGCTGGGCTTACAGGTGTAAGCCATCATGTCC
  1   ------+---------+---------+---------+---------+---------+    60
      CTCGAGCTCGCTAGGGGTGGAGGGTTTCACGACCCGAATGTCCACATTCGGTAGTACAGG

A   R   A   I   P   T   S   Q   S   A   G   L   T   G   V   S   H   H   V   Q -

AGCCGTTCAGATATTCTAGTTGAATTGGAGTTGGTGGGCTAGTACACCTTCTAAATTAAA
 61   ------+---------+---------+---------+---------+---------+   120
      TCGGCAAGTCTATAAGATCAACTTAACCTCAACCACCCGATCATGTGGAAGATTTAATTT

P   F   R   Y   S   S   *   I   G   V   G   G   L   V   H   L   L   N   *   M -

TGAGTAAAGGATTTAGAATGGTGCCTGACACACAGTAGGTGCTACATTCATGTTAGCTAC
121   ------+---------+---------+---------+---------+---------+   180
      ACTCATTTCCTAAATCTTACCACGGACTGTGTGTCATCCACGATGTAAGTACAATCGATG

S   K   G   F   R   M   V   P   D   T   Q   *   V   L   H   S   C   *   L   L -

TATTATAAACCTTTCCTGCCTCTGACTTTCAGGGTCTTGCCCACCACCAGCGATGCCCAG
181   ------+---------+---------+---------+---------+---------+   240
      ATAATATTTGGAAAGGACGGAGACTGAAAGTCCCAGAACGGGTGGTGGTCGCTACGGGTC

L   *   T   F   P   A   S   D   F   Q   G   L   A   H   H   Q   R   C   P   A -

CCCTTGGTAGAGCTTGAACCACCTTCTATAAACAGGATGGCGGTGGAGAGACAGGCCCAG
241   ------+---------+---------+---------+---------+---------+   300
      GGGAACCATCTCGAACTTGGTGGAAGATATTTGTCCTACCGCCACCTCTCTGTCCGGGTC

L   G   R   A   *   T   T   F   Y   K   Q   D   G   G   E   T   G   P   V -

TCCCTGAGCCCATGAGGAGTGTGGCCCCTTCAGGCCCAAAGATGGGGAACATCACTGCAG
301   ------+---------+---------+---------+---------+---------+   360
      AGGGACTCGGGTACTCCTCACACCGGGGAAGTCCGGGTTTCTACCCCTTGTAGTGACGTC

P   E   P   M   R   S   V   A   P   S   G   P   K   M   G   N   I   T   A   D -

ACAACTCCTCGATGAGCTGTACCATCGACCATACCATCCACCAGACGCTGGCCCCGGTGG
361   ------+---------+---------+---------+---------+---------+   420
      TGTTGAGGAGCTACTCGACATGGTAGCTGGTATGGTAGGTGGTCTGCGACCGGGGCCACC

N   S   S   M   S   C   T   I   D   H   T   I   H   Q   T   L   A   P   V   V -

TCTATGTTACCGTGCTGGTGGTGGGCTTCCCGGCCAACTGCCTGTCCCTCTACTTCGGCT
421   ------+---------+---------+---------+---------+---------+   480
      AGATACAATGGCACGACCACCACCCGAAGGGCCGGTTGACGGACAGGGAGATGAAGCCGA

Y   V   T   V   L   V   V   G   F   P   A   N   C   L   S   L   Y   F   G   Y -

ACCTGCAGATCAAGGCCCGGAACGAGCTGGGCGTGTACCTGTGCAACCTGACGGTGGCCG
481   ------+---------+---------+---------+---------+---------+   540
      TGGACGTCTAGTTCCGGGCCTTGCTCGACCCGCACATGGACACGTTGGACTGCCACCGGC

```
     ACCTCTTCTACATCTGCTCGCTGCCCTTCTGGCTGCAGTACGTGCTGCAGCACGACAACT
541  ---------+---------+---------+---------+---------+---------+ 600
     TGGAGAAGATGTAGACGAGCGACGGGAAGACCGACGTCATGCACGACGTCGTGCTGTTGA

L  F  Y  I  C  S  L  P  F  W  L  Q  Y  V  L  Q  H  D  N  W -

GGTCTCACGGCGACCTGTCCTGCCAGGTGTGCCGCATCCTCCTGTACGAGAACATCTACA
601  ---------+---------+---------+---------+---------+---------+ 660
     CCAGAGTGCCGCTGGACAGGACGGTCCACACGGCGTAGGAGGACATGCTCTTGTAGATGT

S  H  G  D  L  S  C  Q  V  C  G  I  L  L  Y  E  N  I  Y  I -

TCAGCGTGGGCTTCCTCTGCTGCATCTCCGTGGACCGCTACCTGGCTGTGGCCCATCCCT
661  ---------+---------+---------+---------+---------+---------+ 720
     AGTCGCACCCGAAGGAGACGACGTAGAGGCACCTGGCGATGGACCGACACCGGGTAGGGA

S  V  G  F  L  C  C  I  S  V  D  R  Y  L  A  V  A  H  P  F -

TCCGCTTCCACCAGTTCCGGACCCTGAAGGCGGCCGTCGGCGTCAGCGTGGTCATCTGGG
721  ---------+---------+---------+---------+---------+---------+ 780
     AGGCGAAGGTGGTCAAGGCCTGGGACTTCCGCCGGCAGCCGCAGTCGCACCAGTAGACCC

R  F  H  Q  F  R  T  L  K  A  A  V  G  V  S  V  V  I  W  A -

CCAAGGAGCTGCTGACCAGCATCTACTTCCTGATGCACGAGGAGGTCATCGAGGACGAGA
781  ---------+---------+---------+---------+---------+---------+ 840
     GGTTCCTCGACGACTGGTCGTAGATGAAGGACTACGTGCTCCTCCAGTAGCTCCTGCTCT

K  E  L  L  T  S  I  Y  F  L  M  H  E  E  V  I  E  D  E  N -

ACCAGCACCGCGTGTGCTTTGAGCACTACCCCATCCAGGCATGGCAGCGCGCCATCAACT
841  ---------+---------+---------+---------+---------+---------+ 900
     TGGTCGTGGCGCACACGAAACTCGTGATGGGGTAGGTCCGTACCGTCGCGCGGTAGTTGA

Q  H  R  V  C  F  E  H  Y  P  I  Q  A  W  Q  R  A  I  N  Y -

ACTACCGCTTCCTGGTGGGCTTCCTCTTCCCCATCTGCCTGCTGCTGGCGTCCTACCAGG
901  ---------+---------+---------+---------+---------+---------+ 960
     TGATGGCGAAGGACCACCCGAAGGAGAAGGGGTAGACGGACGACGACCGCAGGATGGTCC

Y  R  F  L  V  G  F  L  F  P  I  C  L  L  L  A  S  Y  Q  G -

GCATCCTGCGCGCCGTGCGCCGGAGCCACGGCACCCAGAAGAGCCGCAAGGACCAGATCC
961  ---------+---------+---------+---------+---------+---------+ 1020
     CGTAGGACGCGCGGCACGCGGCCTCGGTGCCGTGGGTCTTCTCGGCGTTCCTGGTCTAGG

I  L  R  A  V  R  R  S  H  G  T  Q  K  S  R  K  D  Q  I  Q -

AGCGGCTGGTGCTCAGCACCGTGGTCATCTTCCTGGCCTGCTTCCTGCCCTACCACGTGT
1021 ---------+---------+---------+---------+---------+---------+ 1080
     TCGCCGACCACGAGTCGTGGCACCAGTAGAAGGACCGGACGAAGGACGGGATGGTGCACA

R  L  V  L  S  T  V  V  I  F  L  A  C  F  L  P  Y  H  V  L -

TGCTGCTGGTGCGCAGCGTCTGGGAGGCCAGCTGCGACTTCGCCAAGGGCGTTTTCAACG
1081 ---------+---------+---------+---------+---------+---------+ 1140
     ACGACGACCACGCGTCGCAGACCCTCCGGTCGACGCTGAAGCGGTTCCCGCAAAAGTTGC

```
        CCTACCACTTCTCCCTCCTGCTCACCAGCTTCAACTGCGTCGCCGACCCCGTGCTCTACT
1141    ---------+---------+---------+---------+---------+---------+ 1200
        GGATGGTGAAGAGGGAGGACGAGTGGTCGAAGTTGACGCAGCGGCTGGGGCACGAGATGA

Y  H  F  S  L  L  L  T  S  F  N  C  V  A  D  P  V  L  Y  C -

GCTTCGTCAGCGAGACCACCCACCGGGACCTGGCCCGCCTCCGCGGGGCCTGCCTGGCCT
1201    ---------+---------+---------+---------+---------+---------+ 1260
        CGAAGCAGTCGCTCTGGTGGGTGGCCCTGGACCGGGCGGAGGCGCCCCGGACGGACCGGA

F  V  S  E  T  T  H  R  D  L  A  R  L  R  G  A  C  L  A  F -

TCCTCACCTGCTCCAGGACCGGCCGGGCCAGGGAGGCCTACCCGCTGGGTGCCCCCGAGG
1261    ---------+---------+---------+---------+---------+---------+ 1320
        AGGAGTGGACGAGGTCCTGGCCGGCCCGGTCCCTCCGGATGGGCGACCCACGGGGGCTCC

L  T  C  S  R  T  G  R  A  R  E  A  Y  P  L  G  A  P  E  A -

CCTCCGGGAAAAGCGGGGCCCAGGGTGAGGAGCCCGAGCTGTTGACCAAGCTCCACCCGG
1321    ---------+---------+---------+---------+---------+---------+ 1380
        GGAGGCCCTTTTCGCCCCGGGTCCCACTCCTCGGGCTCGACAACTGGTTCGAGGTGGGCC

S  G  K  S  G  A  Q  G  E  E  P  E  L  L  T  K  L  H  P  A -

CCTTCCAGACCCCTAACTCGCCAGGGTCGGGCGGGTTCCCCACGGGCAGGTTGGCCTAGC
1381    ---------+---------+---------+---------+---------+---------+ 1440
        GGAAGGTCTGGGGATTGAGCGGTCCCAGCCCGCCCAAGGGGTGCCCGTCCAACCGGATCG

F  Q  T  P  N  S  P  G  S  G  G  F  P  T  G  R  L  *  'P -

CTGGGTCCTCCGCGGGTGGCTCCACGTGAGGCCTGAGCCTTCAGCCCACGGGCCTCAGGG
1441    ---------+---------+---------+---------+---------+---------+ 1500
        GACCCAGGAGGCGCCCACCGAGGTGCACTCCGGACTCGGAAGTCGGGTGCCCGGAGTCCC

G  S  S  A  G  G  S  T  *  G  L  S  L  Q  P  T  G  L  R  A -

CCTGCCGCCTCCTGCTTCCCTCGCTGCGGAGGCAGGGAAGCCCCTGTAACTCCGGAAGCC
1501    ---------+---------+---------+---------+---------+---------+ 1560
        GGACGGCGGAGGACGAAGGGAGCGACGCCTCCGTCCCTTCGGGGACATTGAGGCCTTCGG

C  R  L  L  L  P  S  L  R  R  Q  G  S  P  C  N  S  G  S  L -

TGCTCTCGCTTGCTGAGCCCGCTGGGACCGCCGAGGT
1561    ---------+---------+---------+------ 1597
        ACGAGAGCGAACGACTCGGGCGACCCTGGCGGCTCCA

G-PROTEIN COUPLED RECEPTOR HUVCT36

FIELD OF THE INVENTION

This invention relates, in part, to newly identified polynucleotides and polypeptides; variants and derivatives of the polynucleotides and polypeptides; processes for making the polynucleotides and the polypeptides, and their variants and derivatives; agonists and antagonists of the polypeptides; and uses of the polynucleotides, polypeptides, variants, derivatives, agonists and antagonists. In particular, in these and in other regards, the invention relates to polynucleotides and polypeptides of a human G-Protein Coupled Receptor, hereinafter referred to as "HUVCT36".

BACKGROUND OF THE INVENTION

This invention relates to newly identified polynucleotides, polypeptides encoded by such polynucleotides, the use of such polynucleotides and polypeptides, as well as the production of such polynucleotides and polypeptides. More particularly, the polypeptides of the present invention are human 7-transmembrane receptors which resemble platelet-activating factor receptor. The invention also relates to inhibiting or activating the action of such polypeptides.

It is well established that many medically significant biological processes are mediated by proteins participating in signal transduction pathways that involve G-proteins and/or second messengers, e.g., cAMP (Lefkowitz, *Nature*, 1991, 351:353–354). Herein these proteins are referred to as proteins participating in pathways with G-proteins or PPG proteins. Some examples of these proteins include the GPC receptors, such as those for adrenergic agents and dopamine (Kobilka, B. K., et al., *Proc. Natl Acad. Sci., USA*, 1987, 84:46–50; Kobilka, B. K., et al., *Science*, 1987, 238:650–656; Bunzow, J. R., et al., *Nature*, 1988, 336:783–787), G-proteins themselves, effector proteins, e.g., phospholipase C, adenyl cyclase, and phosphodiesterase, and actuator proteins, e.g., protein kinase A and protein kinase C (Simon, M. I., et al., *Science*, 1991, 252:802–8).

For example, in one form of signal transduction, the effect of hormone binding is activation of the enzyme, adenylate cyclase, inside the cell. Enzyme activation by hormones is dependent on the presence of the nucleotide GTP. GTP also influences hormone binding. A G-protein connects the hormone receptor to adenylate cyclase. G-protein was shown to exchange GTP for bound GDP when activated by a hormone receptor. The GTP-carrying form then binds to activated adenylate cyclase. Hydrolysis of GTP to GDP, catalyzed by the G-protein itself, returns the G-protein to its basal, inactive form. Thus, the G-protein serves a dual role, as an intermediate that relays the signal from receptor to effector, and as a clock that controls the duration of the signal.

The membrane protein gene superfamily of G-protein coupled receptors has been characterized as having seven putative transmembrane domains. The domains are believed to represent transmembrane α-helices connected by extracellular or cytoplasmic loops. G-protein coupled receptors include a wide range of biologically active receptors, such as hormone, viral, growth factor and neuroreceptors.

G-protein coupled receptors have been characterized as including these seven conserved hydrophobic stretches of about 20 to 30 amino acids, connecting at least eight divergent hydrophilic loops. The G-protein family of coupled receptors includes dopamine receptors which bind to neuroleptic drugs used for treating psychotic and neurological disorders. Other examples of members of this family include, but are not limited to, calcitonin, adrenergic, endothelin, cAMP, adenosine, muscarinic, acetylcholine, serotonin, histamine, thrombin, kinin, follicle stimulating hormone, opsins, endothelial differentiation gene-1, rhodopsins, odorant, and cytomegalovirus receptors.

Most G-protein coupled receptors have single conserved cysteine residues in each of the first two extracellular loops which form disulfide bonds that are believed to stabilize functional protein structure. The 7 transmembrane regions are designated as TM1, TM2, TM3, TM4, TM5, TM6, and TM7. TM3 has been implicated in signal transduction.

Phosphorylation and lipidation (palmitylation or farnesylation) of cysteine residues can influence signal transduction of some G-protein coupled receptors. Most G-protein coupled receptors contain potential phosphorylation sites within the third cytoplasmic loop and/or the carboxy terminus. For several G-protein coupled receptors, such as the β-adrenoreceptor, phosphorylation by protein kinase A and/or specific receptor kinases mediates receptor desensitization.

For some receptors, the ligand binding sites of G-protein coupled receptors are believed to comprise hydrophilic sockets formed by several G-protein coupled receptor transmembrane domains, said socket being surrounded by hydrophobic residues of the G-protein coupled receptors. The hydrophilic side of each G-protein coupled receptor transmembrane helix is postulated to face inward and form polar ligand binding site. TM3 has been implicated in several G-protein coupled receptors as having a ligand binding site, such as the TM3 aspartate residue. TM5 serines, a TM6 asparagine and TM6 or TM7 phenylalanines or tyrosines are also implicated in ligand binding.

G-protein coupled receptors can be intracellularly coupled by heterotrimeric G-proteins to various intracellular enzymes, ion channels and transporters (see, Johnson et al., *Endoc. Rev.*, 1989, 10:317–331) Different G-protein α-subunits preferentially stimulate particular effectors to modulate various biological functions in a cell. Phosphorylation of cytoplasmic residues of G-protein coupled receptors have been identified as an important mechanism for the regulation of G-protein coupling of some G-protein coupled receptors. G-protein coupled receptors are found in numerous sites within a mammalian host.

The presence of some partially conserved regions in the sequences of members of this gene family has allowed for the use of homologous screening and polymerase chain reaction amplification to isolate receptors. Using these techniques, two closely related G protein-coupled receptor candidates expressed predominantly in human lung tissue, referred to as GPR12A and GPR6C.1, were cloned and sequenced. (An et al. *FEBS Letters*, 1995, 375:121–124. The optimal open reading frame of GPR12A has 1095 bp, which encodes a putative receptor of 365 amino acids. The open reading frame of GPR6C.1 is 1086 bp and encodes a protein of 362 amino acids which is 46.1% identical to GPR12A . The similarities between GPR12A and GPR6C.1 imply that they are receptors for ligands of similar chemical structure or receptor subtypes for the same ligand.

Over the past 15 years, nearly 350 therapeutic agents targeting 7 transmembrane (7 TM) receptors have been successfully introduced onto the market. This indicates that these receptors have an established, proven history as therapeutic targets. Clearly there is a need for identification and characterization of further receptors which can play a role in preventing, ameliorating or correcting dysfunctions or diseases, including, but not limited to, infections such as bacterial, fungal, protozoan and viral infections, particularly infections caused by HIV-1 or HIV-2; pain; cancers; anorexia; bulimia; asthma; Parkinson's disease; acute heart failure; hypotension; hypertension; urinary retention; osteoporosis; angina pectoris; myocardial infarction; ulcers; asthma; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome, among others.

SUMMARY OF THE INVENTION

Toward these ends, and others, it is an object of the present invention to provide polypeptides, inter alia, that have been identified as novel HUVCT36 by homology between the amino acid sequence set out in FIGS. 1A to 1C and known amino acid sequences of other proteins such as human platelet activating factor receptor, angiotensin type 2 receptor, and purinoceptor.

It is a further object of the invention, to provide polynucleotides that encode HUVCT36, particularly polynucleotides that encode the polypeptide herein designated by SEQ ID NO:2.

In a particularly preferred embodiment of this aspect of the invention the polynucleotide comprises the region encoding human HUVCT36 in the sequence set out in FIGS. 1A to 1C.

In accordance with this aspect of the present invention there is provided an isolated nucleic acid molecule encoding a mature polypeptide expressible from the human cDNA contained in ATCC Deposit No. 98156.

In accordance with this aspect of the invention there are provided isolated nucleic acid molecules encoding human HUVCT36, including mRNAs, cDNAs, genomic DNAs and fragments, in further embodiments of this aspect of the invention, biologically, diagnostically, clinically or therapeutically useful variants, analogs or derivatives thereof, including fragments of the variants, analogs and derivatives.

Among the particularly preferred embodiments of this aspect of the invention are naturally occurring allelic variants of human HUVCT36.

It also is an object of the invention to provide HUVCT36 polypeptides, particularly human HUVCT36 polypeptides, that may be employed for therapeutic purposes, for example, to treat infections, such as bacterial, fungal, protozoan and viral infections, particularly infection caused by HIV-1 or HIV-2; pain; cancers; anorexia; bulimia; asthma; Parkinson's disease; acute heart failure; hypotension; hypertension; urinary retention; osteoporosis; angina pectoris; myocardial infarction; ulcers; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome, among others.

In accordance with this aspect of the invention there are provided novel polypeptides of human origin referred to herein as HUVCT36 as well as biologically, diagnostically or therapeutically useful fragments, variants and derivatives thereof, variants and derivatives of the fragments, and analogs of the foregoing.

Among the particularly preferred embodiments of this aspect of the invention are variants of human HUVCT36 encoded by naturally occurring alleles of the human HUVCT36 gene.

In accordance with another aspect of the present invention there are provided methods of screening for compounds which bind to and activate or inhibit activation of the receptor polypeptides of the present invention and for receptor ligands.

It is another object of the invention to provide a process for producing the aforementioned polypeptides, polypeptide fragments, variants and derivatives, fragments of the variants and derivatives, and analogs of the foregoing. In a preferred embodiment of this aspect of the invention there are provided methods for producing the aforementioned HUVCT36 polypeptides comprising culturing host cells having expressibly incorporated therein an exogenously-derived human HUVCT36-encoding polynucleotide under conditions for expression of human HUVCT36 in the host; expressing the polypeptide; and then recovering the expressed polypeptide.

In accordance with another object the invention, there are provided products, compositions, processes and methods that utilize the aforementioned polypeptides and polynucleotides for research, biological, clinical and therapeutic purposes, inter alia.

In accordance with certain preferred embodiments of this aspect of the invention, there are provided products, compositions and methods, inter alia, for, among other things: assessing HUVCT36 expression in cells by determining HUVCT36 polypeptides or HUVCT36-encoding mRNA; to treat infections, such as bacterial, fungal, protozoan and viral infections, particularly infection caused by HIV-1 or HIV-2 ; pain; cancers; anorexia; bulimia; asthma; Parkinson's disease; acute heart failure; hypotension; hypertension; urinary retention; osteoporosis; angina pectoris; myocardial infarction; ulcers; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome; among others, in vitro, ex vivo or in vivo by exposing cells to HUVCT36 polypeptides or polynucleotides as disclosed herein; assaying genetic variation and aberrations, such as defects, in HUVCT36 genes; and administering a HUVCT36 polypeptide or polynucleotide to an organism to augment HUVCT36 function or remediate HUVCT36 dysfunction.

In accordance with still another embodiment of the present invention, there is provided a process of using such activating compounds to stimulate the receptor polypeptide of the present invention for the treatment of conditions related to the under-expression of HUVCT36.

In accordance with another aspect of the present invention, there is provided a process of using such inhibiting compounds for treating conditions associated with over-expression of the HUVCT36.

In accordance with yet another aspect of the present invention, there is provided nonnaturally occurring synthetic, isolated and/or recombinant HUVCT36 polypeptides which are fragments, consensus fragments and/or sequences having conservative amino acid substitutions, of at least one domain of the HUVCT36 of the present invention, such that the receptor may bind HUVCT36 ligands, or which may also modulate, quantitatively or qualitatively, HUVCT36 ligand binding.

In accordance with still another aspect of the present invention, there are provided synthetic or recombinant HUVCT36 polypeptides, conservative substitution and derivatives thereof, antibodies thereto, anti-idiotype antibodies, compositions and methods that can be useful as potential modulators of HUVCT36 function, by binding to ligands or modulating ligand binding, due to their expected biological properties, which may be used in diagnostic, therapeutic and/or research applications.

It is still another object of the present invention to provide synthetic, isolated or recombinant polypeptides which are designed to inhibit or mimic various HUVCT36 or fragments thereof, as receptor types and subtypes.

In accordance with certain preferred embodiments of this and other aspects of the invention there are provided probes that hybridize to human HUVCT36 sequences.

In certain additional preferred embodiments of this aspect of the invention there are provided antibodies against HUVCT36 polypeptides. In certain particularly preferred embodiments in this regard, the antibodies are highly selective for human HUVCT36.

In accordance with another aspect of the present invention, there are provided HUVCT36 agonists. Among preferred agonists are molecules that mimic HUVCT36, that bind to HUVCT36-binding molecules or receptor molecules, and that elicit or augment HUVCT36-induced responses. Also among preferred agonists are molecules that interact with HUVCT36 or HUVCT36 polypeptides, or with other modulators of HUVCT36 activities, and thereby potentiate or augment an effect of HUVCT36 or more than one effect of HUVCT36.

In accordance with yet another aspect of the present invention, there are provided HUVCT36 antagonists. Among preferred antagonists are those which mimic HUVCT36 so as to bind to HUVCT36 receptor or binding molecules but not elicit a HUVCT36-induced response or more than one HUVCT36-induced response. Also among preferred antagonists are molecules that bind to or interact with HUVCT36 so as to inhibit an effect of HUVCT36 or more than one effect of HUVCT36 or which prevent expression of HUVCT36.

In a further aspect of the invention, there are provided compositions comprising a HUVCT36 polynucleotide or a HUVCT36 polypeptide for administration to cells in vitro, to cells ex vivo and to cells in vivo, or to a multicellular organism. In certain particularly preferred embodiments of this aspect of the invention, the compositions comprise a HUVCT36 polynucleotide for expression of a HUVCT36 polypeptide in a host organism for treatment of disease. Particularly preferred in this regard is expression in a human patient for treatment of a dysfunction associated with aberrant endogenous activity of HUVCT36.

Other objects, features, advantages and aspects of the present invention will become apparent to those of skill in the art from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

BRIEF DESCRIPTION OF THE DRAWINGS

The following drawings depict certain embodiments of the invention. They are illustrative only and do not limit the invention otherwise disclosed herein.

FIG. 1A shows the beginning of the nucleotide (SEQ ID NO:1) and deduced amino acid sequence (SEQ ID NO:2) of human HUVCT36.

FIG. 1B shows a continuation of the nucleotide (SEQ ID NO:1) and deduced amino acid sequence (SEQ ID NO:2) of human HUTVCT36.

FIG. 1C shows the end of the nucleotide (SEQ ID NO:1) and deduced amino acid sequence (SEQ ID NO:2) of humau HUVCT36.

FIG. 2 shows a comparison of the amino acid sequence of GPR12A (SEQ ID NO:3) with the deduced amino acid sequence of human HUVCT36 (SEQ ID NO:2). Amino acids designated by italics represent differences in the sequences.

GLOSSARY

The following illustrative explanations are provided to facilitate understanding of certain terms used frequently herein, particularly in the examples. The explanations are provided as a convenience and are not meant to limit the invention.

"Digestion" of DNA refers to catalytic cleavage of a DNA with an enzyme such as, but not limited to, a restriction enzyme that acts only at certain sequences in the DNA. The various restriction enzymes referred to herein are commercially available and their reaction conditions, cofactors and other requirements for use are known and routine to the skilled artisan.

For analytical purposes, typically, 1 microgram of plasmid or DNA fragment is digested with about 2 units of enzyme in about 20 microliters of reaction buffer. For the purpose of isolating DNA fragments for plasmid construction, typically 5 to 50 micrograms of DNA are digested with 20 to 250 units of enzyme in proportionately larger volumes.

Appropriate buffers and substrate amounts for particular restriction enzymes are described in standard laboratory manuals, such as those referenced below, and they are specified by commercial suppliers.

Incubation times of about 1 hour at 37° C. are ordinarily used, but conditions may vary in accordance with standard procedures, the supplier's instructions and the particulars of the reaction. After digestion, reactions may be analyzed, and fragments may be purified by electrophoresis through an agarose or polyacrylamide gel, using well known methods that are routine to those skilled in the art.

"Genetic element" generally means a polynucleotide comprising a region that encodes a polypeptide or a region that regulates replication, transcription or translation or other processes important to expression of the polypeptide in a host cell, or a polynucleotide comprising both a region that encodes a polypeptide and a region operably linked thereto that regulates expression.

Genetic elements may be comprised within a vector that replicates as an episomal element; that is, as a molecule physically independent of the host cell genome. They may be comprised within mini-chromosomes, such as those that arise during amplification of transfected DNA by methotrexate selection in eukaryotic cells. Genetic elements may also be comprised within a host cell genome; not in their natural state but, rather, following manipulation such as isolation, cloning and introduction into a host cell in the form of purified DNA or in a vector, among others.

"Isolated" means altered "by the hand of man" from its natural state; i.e., that, if it occurs in nature, it has been changed or removed from its original environment, or both. For example, a naturally occurring polynucleotide or a polypeptide naturally present in a living animal in its natural state is not "isolated," but the same polynucleotide or polypeptide separated from the coexisting materials of its natural state is "isolated", as the term is employed herein. With respect to polynucleotides, for example, the term isolated means that it is separated from the chromosome and cell in which it naturally occurs.

As part of or following isolation, such polynucleotides can be joined to other polynucleotides, such as DNAs, for mutagenesis, to form fusion proteins, and for propagation or expression in a host, for instance. The isolated polynucleotides, alone or joined to other polynucleotides such as vectors, can be introduced into host cells, in culture or in whole organisms. Introduced into host cells in culture or in whole organisms, such DNAs still would be isolated, as the term is used herein, because they would not be in their naturally occurring form or environment. Similarly, the polynucleotides and polypeptides may occur in a composition, such as media; formulations; solutions for introduction of polynucleotides or polypeptides, for example, into cells; or compositions or solutions for chemical or enzymatic reactions, for instance, which are not naturally occurring compositions, and, therein remain isolated polynucleotides or polypeptides within the meaning of that term as it is employed herein.

"Ligation" refers to the process of forming phosphodiester bonds between two or more polynucleotides, which most often are double stranded DNAs. Techniques for ligation are well known to the art and protocols for ligation are described in standard laboratory manuals and references, such as, for instance, Sambrook et al., MOLECULAR CLONING, A LABORATORY MANUAL, 2nd Ed.; Cold Spring Harbor Laboratory Press, Cold Spring Harbor, N.Y. (1989), hereinafter referred to as Sambrook et al.

"Oligonucleotide(s)" refers to relatively short polynucleotides. Often the term refers to single-stranded deoxyribonucleotides, but it can refer as well to single- or double-stranded ribonucleotides, RNA:DNA hybrids and double-stranded DNAs, among others.

Oligonucleotides, such as single-stranded DNA probe oligonucleotides, often are synthesized by chemical methods, such as those implemented on automated oligonucleotide synthesizers. However, oligonucleotides can be made by a variety of other methods, including in vitro recombinant DNA-mediated techniques and by expression of DNAs in cells and organisms.

Initially, chemically synthesized DNAs typically are obtained without a 5' phosphate. The 5' ends of such oligonucleotides are not substrates for phosphodiester bond formation by ligation reactions that employ DNA ligases typically used to form recombinant DNA molecules. Where ligation of such oligonucleotides is desired, a phosphate can be added by standard techniques, such as those that employ a kinase and ATP.

The 3' end of a chemically synthesized oligonucleotide generally has a free hydroxyl group and, in the presence of a ligase, such as T4 DNA ligase, will readily form a phosphodiester bond with a 5' phosphate of another polynucleotide, such as another oligonucleotide. As is well known, this reaction can be prevented selectively, where desired, by removing the 5' phosphates of the other polynucleotide(s) prior to ligation.

"Plasmids" are genetic elements that are stably inherited without being a part of the chromosome of their host cell. They may be comprised of DNA or RNA and may be linear or circular. Plasmids code for molecules that ensure their replication and stable inheritance during cell replication and may encode products of considerable medical, agricultural and environmental importance. For example, they code for toxins that greatly increase the virulence of pathogenic bacteria. They can also encode genes that confer resistance to antibiotics. Plasmids are widely used in molecular biology as vectors used to clone and express recombinant genes. Plasmids generally are designated herein by a lower case "p" preceded and/or followed by capital letters and/or numbers, in accordance with standard naming conventions that are familiar to those of skill in the art. Starting plasmids disclosed herein are either commercially available, publicly available, or can be constructed from available plasmids by routine application of well known, published procedures. Many plasmids and other cloning and expression vectors that can be used in accordance with the present invention are well known and readily available to those of skill in the art. Moreover, those of skill may routinely construct any number of other plasmids suitable for use in the invention. The properties, construction and use of such plasmids, as well as other vectors, in the present invention will be readily apparent to those of skill from the present disclosure.

"Polynucleotide(s)" generally refers to any polyribonucleotide or polydeoxribonucleotide, which may be unmodified RNA or DNA or modified RNA or DNA. Thus, for instance, polynucleotides, as used herein, refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, polynucleotide, as used herein, refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide.

As used herein, the term polynucleotide includes DNAs or RNAs as described above that contain one or more modified bases. Thus, DNAs or RNAs with backbones modified for stability or for other reasons are polynucleotides as that term is intended herein. Moreover, DNAs or RNAs comprising unusual bases, such as inosine, or modified bases, such as tritylated bases, to name just two examples, are polynucleotides as the term is used herein.

It will be appreciated that a great variety of modifications have been made to DNA and RNA that serve many useful purposes known to those of skill in the art. The term polynucleotide, as it is employed herein, embraces such chemically, enzymatically or metabolically modified forms of polynucleotides, as well as the chemical forms of DNA and RNA characteristic of viruses and cells, including inter alia simple and complex cells.

"Polypeptides", as used herein, includes all polypeptides as described below. The basic structure of polypeptides is well known and has been described in innumerable textbooks and other publications in the art. In this context, the term is used herein to refer to any peptide or protein comprising two or more amino acids joined to each other in a linear chain by peptide bonds. As used herein, the term refers to both short chains, which are also commonly referred to in the art as peptides, oligopeptides and oligomers, for example, and to longer chains, which generally are referred to in the art as proteins, of which there are many types.

It will be appreciated that polypeptides often contain amino acids other than the 20 amino acids commonly referred to as the 20 naturally occurring amino acids, and that many amino acids, including the terminal amino acids, may be modified in a given polypeptide, either by natural processes, such as processing and other post-translational modifications, or by chemical modification techniques which are well known to the art. Even the common modifications that occur naturally in polypeptides are too numerous to list exhaustively here, but they are well described in basic texts and in more detailed monographs, as well as in a voluminous research literature, and thus are well known to those of skill in the art. Examples of known modifications which may be present in polypeptides of the present invention, include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. Such modifications are well known to those of skill and have been described in great detail in the scientific literature. Several particularly common modifications such as glycosylation, lipid attachment, sulfation, gamma-carboxylation of glutamic acid residues, hydroxylation and ADP-ribosylation, for instance, are described in most basic texts such as PROTEINS—STRUCTURE AND MOLECULAR PROPERTIES, 2nd Ed., T. E. Creighton, W. H. Freeman and Company, New York (1993). Detailed reviews are also available on this subject. See e.g. Wold, F., Posttranslational Protein Modifications: Perspectives and Prospects, pages 1–12 in POSTTRANSLATIONAL COVALENT MODIFICATION OF PROTEINS, B. C. Johnson, Ed., Academic Press, New York (1983); Seifter et al, *Meth. Enzymol.*, 1990, 182:626–646 and Rattan et al, *Ann. N.Y. Acad. Sci.*, 1992, 663:48–62.

It will be appreciated, as is well known and as noted above, that polypeptides are not always entirely linear. For instance, polypeptides may be branched as a result of ubiquitination, and they may be circular, with or without branching, generally as a result of posttranslation events, including natural processing events and events brought about by human manipulation which do not occur naturally. Circular, branched and branched circular polypeptides may be synthesized by non-translational natural processes and entirely by synthetic methods.

Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides and such modifications may be present in polypeptides of the present invention, as well. For instance, the amino terminal residue of polypeptides made in *E. coli*, prior to processing, almost invariably will be N-formylmethionine.

The modifications that occur in a polypeptide often will be a function of how it is made. For polypeptides made by expressing a cloned gene in a host, for instance, the nature and extent of the modifications in large part will be determined by the host cell's posttranslational modification capacity and the modification signals present in the polypeptide amino acid sequence. For instance, as is well known, glycosylation often does not occur in bacterial hosts such as *E. coli*. Accordingly, when glycosylation is desired, a polypeptide should be expressed in a glycosylating host, generally a eukaryotic cell. Insect cells often carry out the same posttranslational glycosylations as mammalian cells and, for this reason, insect cell expression systems have been developed to express efficiently mammalian proteins having the native patterns of glycosylation, inter alia. Similar considerations apply to other modifications.

It will be appreciated that the same type of modification may be present in the same or varying degree at several sites in a given polypeptide. Also, a given polypeptide may contain many types of modifications.

In general, as used herein, the term polypeptide encompasses all such modifications, particularly those that are present in polypeptides synthesized by expressing a polynucleotide in a host cell.

"Variant(s)" of polynucleotides or polypeptides, as the term is used herein, are polynucleotides or polypeptides that differ from a reference polynucleotide or polypeptide, respectively. Variants in this sense are described below and elsewhere in the present disclosure in greater detail. Variants include polynucleotides that differ in nucleotide sequence from another, reference polynucleotide. Generally, differences are limited so that the nucleotide sequences of the reference and the variant are closely similar overall and, in many regions, identical.

As noted below, changes in the nucteotide sequence of the variant may be silent. That is, they may not alter the amino acids encoded by the polynucleotide. Where alterations are limited to silent changes of this type, a variant will encode a polypeptide with the same amino acid sequence as the reference. As also noted below, changes in the nucleotide sequence of the variant may alter the amino acid sequence of a polypeptide encoded by the reference polynucleotide. Such nucleotide changes may result in amino acid substitutions, additions, deletions, fusions and truncations in the polypeptide encoded by the reference sequence, as discussed below.

Variants also include polypeptides that differ in amino acid sequence from another, reference polypeptide. Generally, differences are limited so that the sequences of the reference and the variant are closely similar overall and, in many regions, identical. A variant and reference polypeptide may differ in amino acid sequence by one or more substitutions, additions, deletions, or fusions, which may be present in any combination.

"Fusion proteins" as the term is used herein, are proteins encoded by two, often unrelated, fused genes or fragments thereof. EP-A-O 464 533 (Canadian counterpart 2045869) discloses fusion proteins comprising various portions of constant region of immunoglobin molecules together with another human protein or part thereof. In many cases, employing an immunoglobulin Fc region as a part of a fusion protein is advantageous for use in therapy and diagnosis resulting in, for example, improved pharmacokinetic properties (EP-A 0232 262). On the other hand, for some uses it would be desirable to be able to delete the Fc part after the fusion protein has been expressed, detected and purified. Accordingly, it may be desirable to link the two components of the fusion protein with a chemically or enzymatically cleavable linking region. This is the case when the Fc portion proves to be a hindrance to use in therapy and diagnosis, for example when the fusion protein is to be used as an antigen for immunizations. In drug discovery, for example, human proteins, such as, shIL5-α, had been fused with Fc portions for use in high-throughput screening assays to identify antagonists of hIL-5. See D. Bennett et al., *Journal of Molecular Recognition*, 1995, 8, 52–58 and K. Johanson et al., *The Journal of Biological Chemistry*, 1995, 270(16):9459–9471.

Thus, this invention also relates to genetically engineered soluble fusion proteins comprised of HUVCT36, or a portion thereof, and of various portions of the constant regions of heavy or light chains of immunoglobulins of various subclasses (IgG, IgM, IgA, IgE). Preferred as an immunoglobulin is the constant part of the heavy chain of human IgG, particularly IgG1, where fusion takes place at the hinge region. In a particular embodiment, the Fc part can be removed simply by incorporation of a cleavage sequence which can be cleaved with blood clotting factor Xa. Furthermore, this invention relates to processes for the preparation of these fusion proteins by genetic engineering, and to the use thereof for diagnosis and therapy. A further aspect of the invention relates to polynucleotides encoding such fusion proteins.

Membrane bound receptors are particularly useful in the formation of fusion proteins. Such receptors are generally characterized as possessing three distinct structural regions: an extracellular domain; a transmembrane domain; and a cytoplasmic domain. This invention contemplates the use of one or more of these regions as components of a fusion protein. Examples of such fusion protein technology can be found in WO94/29458 and WO94/22914.

"Binding molecules" (or otherwise called "interaction molecules" or "receptor component factors") refer to molecules, including ligands that specifically bind to or interact with receptor polypeptides of the present invention. Such binding molecules are a part of the present invention. Binding molecules may also be non-naturally occurring, such as antibodies and antibody-derived reagents that bind specifically to polypeptides of the invention.

As known in the art, "similarity" between two polypeptides is determined by comparing the amino acid sequence and its conserved amino acid substitutes of one polypeptide to the sequence of a second polypeptide. Moreover, also known in the art is "identity" which means the degree of sequence relatedness between two polypeptide or two polynucleotide sequences as determined by the identity of the match between two lengths of such sequences. Both identity and similarity can be readily calculated in accordance with published procedures. See e.g. COMPUTATIONAL MOLECULAR BIOLOGY, Lesk, A.M., ed., Oxford University Press, New York, 1988; BIOCOMPUTING: INFORMATICS AND GENOME PROJECTS, Smith, D. W., ed., Academic Press, New York, 1993; COMPUTER ANALYSIS OF SEQUENCE DATA, PART I, Griffin, A. M., and Griffin, H. G., eds., Humana Press, New Jersey, 1994; SEQUENCE ANALYSIS IN MOLECULAR BIOLOGY, von Heinje, G., Academic Press, 1987; and SEQUENCE ANALYSIS PRIMER, Gribskov, M. and Devereux, J., eds., M Stockton Press, New York, 1991. There exist a number of methods to measure identity and similarity between two polynucleotide or polypeptide sequences and the terms "identity" and "similarity" are well known to skilled artisans (Carillo, H. and Lipman, D., SIAM *J. Applied Math.*, 1988, 48:1073). Methods commonly employed to determine identity or similarity between two sequences include, but are not limited to, those disclosed in GUIDE TO HUGE COMPUTERS, Martin J. Bishop, ed., Academic Press, San Diego, 1994, and Carillo, H. and Lipman, D., *SIAM J. Applied Math.*, 1988, 48:1073. Preferred methods to determine identity are designed to give the largest match between the two sequences tested. Methods to determine identity and similarity are also codified in computer programs. Preferred computer programs to determine identity and similarity between two sequences include, but are not limited to, GCG program package (Devereux, J., et al., *Nucleic Acids Research*, 1984, 12(1):387), BLASTP, BLASTN, and FASTA (Atschul, S. F. et al.,*J. Molec. Biol.*, 1990, 215:403).

DETAILED DESCRIPTION OF THE INVENTION

The present invention relates to novel HUVCT36 polypeptides and polynucleotides, among other things, as described in greater detail below. In particular, the invention relates to polypeptides and polynucleotides of a novel human HUVCT36, which is related by amino acid sequence homology to human platelet activating factor, angiotensin type 2 receptor and purinoceptor. The invention relates especially to HUVCT36 having the nucleotide and amino acid sequences set out in FIGS. 1A, 1B and 1C, and to the HUVCT36 nucleotide sequences of the human cDNA of ATCC DEPOSIT NO. 98156, herein referred to as "the deposited clone" or as the "cDNA of the deposited clone", and to the amino acid sequences encoded thereby. It will be appreciated that the nucleotide and amino acid sequences set out in FIGS. 1A, 1B and 1C are obtained by sequencing the cDNA of the deposited clone. Hence, the sequence of the deposited clone is controlling as to any discrepancies between the two and any reference to the sequences of FIGS. 1A, 1B and 1C includes a reference to the sequence of the human cDNA of the deposited clone.

Polynucleotides

In accordance with one aspect of the present invention, there are provided isolated polynucleotides which encode the HUVCT36 polypeptide having the deduced amino acid sequence of FIGS. 1A, 1B and 1C, SEQ ID NO:2.

Using the information provided herein, such as the polynucleotide sequence set out in FIGS. 1A, 1B and 1C, SEQ ID NO:1, a polynucleotide of the present invention encoding human HUVCT36 may be obtained using standard cloning and screening procedures, such as those for cloning cDNAs using MRNA from cells from placental tissue as starting material. Illustrative of the invention, the polynucleotide set out in FIGS. 1A, 1B and 1C was discovered in a cDNA library derived from cells of human placental tissue. More specifically, a human genomic library prepared from placental tissue was screened under low stringency hybridization conditions using portions of human α1C-adrenoceptor and 5HT7 receptor cDNAs as hybridization probes. Fifteen strongly hybridizing genomic clones were isolated by plaque dilution purification. DNA was isolated and analyzed by restriction enzyme digestion with Sac I. The Sac I digested DNA fragments were size fractionated using gel electrophoresis. The DNA fragments were then transferred to a nitrocellulose membrane which was hybridized with the same cDNA probes used to screen the human genomic library. A strongly hybridizing fragment with an approximate size of 3 kilobases was subcloned and characterized by DNA sequencing. This clone is designated HUVCT36.

Human HUVCT36 of the invention is structurally related to other proteins of the G-protein coupled receptor family, as shown by the results of sequencing the cDNA encoding human HUVCT36 in the deposited clone. For example, HUVCT36 contains seven hydrophobic regions of approximately 20–30 amino acids each, which are believed to represent membrane spanning domains providing the 7 transmembrane structural topology found among the G-protein linked superfamily of receptors. The cDNA sequence obtained is set out in FIGS. 1A, 1B and 1C, and as SEQ ID NO:1. It contains an open reading frame encoding a protein of 375 amino acids with a deduced molecular weight of about 42 kDa. HUVCT36 of FIGS. 1A, 1B and 1C has about 30.8% identity over its entirety with human platelet activating factor. The protein also shares significant homology with other 7 transmembrane G-protein coupled receptors including, but not limited to, angiotensin type 2 receptor and purinoceptor. When comparing the nucleotide sequence of HUVCT36 to sequence in Genbank, it was found that HUV36CT shares 99.4% homology with the clone GPR12A, a proposed G-protein coupled receptor (An et al. *FEBS Letter*, 1995, 375:121–125). GPR12A has been reverse translated. In contrast to HUVCT36, the open reading frame of GPR12A is 365 amino acids. A comparison of the deduced amino acid sequence of HUVCT36 with that of GPR12A is shown in FIG. 2. Differences between amino acids in these two proteins are italicized. Further, HUVCT36 has an upstream methionine which is believed to be the correct start site of this gene. The comparison to Genbank sequences also revealed a 63.7% homology between HUVCT36 and GPR4, a published orphan G-protein coupled receptor.

Polynucleotides of the present invention may be in the form of RNA, such as mRNA, or in the form of DNA, including, for instance, cDNA and genomic DNA obtained by cloning or produced by chemical synthetic techniques or by a combination thereof. The DNA may be double-stranded or single-stranded. Single-stranded DNA may be the coding strand, also known as the sense strand, or it may be the non-coding strand, also referred to as the anti-sense strand.

The coding sequence which encodes the polypeptide may be identical to the coding sequence of the polynucleotide shown in FIGS. 1A, 1B and 1C, SEQ ID NO:1. It may also be a polynucleotide with a different sequence, which, as a result of the redundancy (degeneracy) of the genetic code, also encodes the polypeptide of FIGS. 1A, 1B and 1C (SEQ ID NO:2).

Polynucleotides of the present invention which encode the polypeptide of FIGS. 1A, 1B and 1C may include, but are not limited to, the coding sequence for the mature polypeptide, by itself; the coding sequence for the mature polypeptide and additional coding sequences, such as those encoding a leader or secretory sequence, such as a preprotein, or proprotein or preproprotein sequence; the coding sequence of the mature polypeptide, with or without the aforementioned additional coding sequences, together with additional, non-coding sequences, including, but not limited to, introns and non-coding 5' and 3' sequences, such as the transcribed, non-translated sequences that play a role in transcription and mRNA processing, including splicing and polyadenylation signals, for example, for ribosome binding and stability of mRNA. Coding sequences which provide additional functionalities may also be incorporated into the polypeptide. Thus, for instance, the polypeptide may be fused to a marker sequence, such as a peptide, which facilitates purification of the fused polypeptide. In certain preferred embodiments of this aspect of the invention, the marker sequence is a hexa-histidine peptide, such as the tag provided in the pQE vector (Qiagen, Inc.), among others, many of which are commercially available. As described in Gentz et al., *Proc. Natl Acad. Sci. USA*, 1989, 86:821–824 for instance, hexa-histidine provides for convenient purification of the fusion protein. The HA tag corresponding to an epitope derived of influenza hemagglutinin protein (Wilson et al., *Cell*, 1984, 37:767) is also useful.

In accordance with the foregoing, the term "polynucleotide encoding a polypeptide" as used herein encompasses polynucleotides which include, by virtue of the redundancy of the genetic code, any sequence encoding a polypeptide of the present invention, particularly the human HUVCT36 having the amino acid sequence set forth in FIGS. 1A, 1B and 1C. The term also encompasses polynucleotides that include a single continuous region or discontinuous regions encoding the polypeptide (for example, interrupted by introns) together with additional regions, that also may contain coding and/or non-coding sequences.

The present invention further relates to variants of the herein above described polynucleotides which encode for fragments, analogs and derivatives of the polypeptide having the deduced amino acid sequence of FIGS. 1A, 1B and 1C. A variant of the polynucleotide may be a naturally occurring variant such as a naturally occurring allelic variant, or it may be a variant that is not known to occur naturally. Such non-naturally occurring variants of the polynucleotide may be made by mutagenesis techniques, including those applied to polynucleotides, cells or organisms.

Among variants in this regard are variants that differ from the aforementioned polynucleotides by nucleotide substitutions, deletions or additions. The substitutions, deletions or additions may involve one or more nucleotides. The variants may be altered in coding or non-coding regions or both. Alterations in the coding regions may produce conservative or non-conservative amino acid substitutions, deletions or additions.

Among the particularly preferred embodiments of the invention in this regard are polynucleotides encoding polypeptides having the amino acid sequence of HUVCT36 set out in FIGS. 1A, 1B and 1C; variants, analogs, derivatives and fragments thereof, and fragments of the variants, analogs and derivatives.

Further, particularly preferred in this regard are polynucleotides encoding HUVCT36 variants, analogs, derivatives and fragments, and variants, analogs and derivatives of the fragments, which have the amino acid sequence of the HUVCT36 polypeptide of FIGS. 1A, 1B and 1C in which several, a few, 5 to 10, 1 to 5, 1 to 3, 2, 1 or no amino acid residues are substituted, deleted or added, in any combination. Especially preferred among these are silent substitutions, additions and deletions, which do not alter the properties and activities of HUVCT36. Also especially preferred in this regard are conservative substitutions. Most highly preferred are polynucleotides encoding polypeptides having the amino acid sequence of FIGS. 1A, 1B and 1C, SEQ ID NO:2, without substitutions.

Particularly preferred embodiments in this respect, moreover, are polynucleotides which encode polypeptides which retain substantially the same biological function or activity as the mature polypeptide encoded by the cDNA of FIGS. 1A, 1B and 1C.

The present invention further relates to polynucleotides that hybridize to the herein above-described sequences. In this regard, the present invention especially relates to polynucleotides which hybridize under stringent conditions to the herein above-described polynucleotides. As herein used, the term "stringent conditions" means hybridization will occur only if there is at least 95% and preferably at least 97% identity between the sequences.

As discussed additionally herein regarding polynucleotide assays of the invention, for instance, polynucleotides of the invention as discussed above, may be used as hybridization probes for cDNA and genomic DNA, to isolate full-length cDNAs and genomic clones encoding HUVCT36 and to isolate cDNA and genomic clones of other genes that have a high sequence similarity to the human HUVCT36 gene. Such probes generally will comprise at least 15 nucleotides. Preferably, such probes will have at least 30 nucleotides and may have at least 50 nucleotides. Particularly preferred probes will range between 30 and 50 nucleotides.

For example, the coding region of the HUVCT36 gene may be isolated by screening using the known DNA sequence to synthesize an oligonucleotide probe. A labeled oligonucleotide having a sequence complementary to that of a gene of the present invention is then used to screen a library of human cDNA, genomic DNA or mRNA to determine the members of the library to which the probe hybridizes to.

The polynucleotides and polypeptides of the present invention may be employed as research reagents and materials for discovery of treatments and diagnostics to human disease, as further discussed herein relating to polynucleotide assays.

The polynucleotides may encode a polypeptide which is the mature protein plus additional amino or carboxyl-terminal amino acids, or amino acids interior to the mature polypeptide (when the mature form has more than one polypeptide chain, for instance). Such sequences may play a role in processing of a protein from precursor to a mature form, may facilitate protein trafficking, may prolong or shorten protein half-life or may facilitate manipulation of a protein for assay or production, among other things. As generally is the case in situ, the additional amino acids may be processed away from the mature protein by cellular enzymes.

A precursor protein, having the mature form of the polypeptide fused to one or more prosequences may be an inactive form of the polypeptide. When prosequences are removed such inactive precursors generally are activated. Some or all of the prosequences may be removed before activation. Generally, such precursors are called proproteins.

In sum, a polynucleotide of the present invention may encode a mature protein, a mature protein plus a leader sequence (which may be referred to as a preprotein), a precursor of a mature protein having one or more prosequences which are not the leader sequences of a preprotein, or a preproprotein, which is a precursor to a proprotein, having a leader sequence and one or more prosequences, which generally are removed during processing steps that produce active and mature forms of the polypeptide.

Deposited Materials

A deposit containing a human HUVCT36 cDNA has been made with the American Type Culture Collection, 12301 Park Lawn Drive, Rockville, Md. 20852, USA, on Aug. 24, 1996, and assigned ATCC Deposit No. 98156. The human cDNA deposit is referred to herein as "the deposited clone" or as "the cDNA of the deposited clone."

The deposited material comprises *E. coli* DH5αHUVCT36pBluescript (Stratagene, La Jolla, Calif.) that contains the full length HUVCT36 cDNA.

The deposit has been made under the terms of the Budapest Treaty on the international recognition of the deposit of microorganisms for purposes of patent procedure. The strain will be irrevocably and without restriction or condition released to the public upon the issuance of a patent. The deposit is provided merely as convenience to those of skill in the art and is not an admission that a deposit is required for enablement, such as that required under 35 U.S.C. §112.

The sequence of the polynucleotides contained in the deposited material, as well as the amino acid sequence of the polypeptide encoded thereby, are controlling in the event of any conflict with any description of sequences herein.

A license may be required to make, use or sell the deposited materials. No such license is hereby granted.

Polypeptides

The present invention further relates to a human HUVCT36 polypeptide which has the deduced amino acid sequence of FIGS. 1A, 1B and 1C, SEQ ID NO:2.

The invention also relates to fragments, analogs and derivatives of these polypeptides. The terms "fragment," "derivative" and "analog" when referring to the polypeptide of FIGS. 1A, 1B and 1C, means a polypeptide which retrains essentially the same biological function or activity as such polypeptide, i.e. functions as a HUVCT36, or retains the ability to bind the ligand or the binding molecules even though the polypeptide does not function as a HUVCT36, for example, a soluble form of the receptor. Thus, an analog includes, for example, a proprotein which can be activated by cleavage of the proprotein portion to produce an active mature polypeptide.

The polypeptide of the present invention may be a recombinant polypeptide, a natural polypeptide or a synthetic polypeptide. In certain preferred embodiments, it is a recombinant polypeptide.

The fragment, derivative or analog of the polypeptide of FIGS. 1A, 1B and 1C may be (i) one in which one or more of the amino acid residues are substituted with a conserved or non-conserved amino acid residue (preferably a conserved amino acid residue) and such substituted amino acid residue may or may not be one encoded by the genetic code, (ii) one in which one or more of the amino acid residues includes a substituent group, (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

Among the particularly preferred embodiments of the invention in this regard are polypeptides having the amino acid sequence of HUVCT36 set out in FIGS. 1A, 1B and 1C, variants, analogs, derivatives and fragments thereof, and variants, analogs and derivatives of the fragments. Further particularly preferred embodiments of the invention in this regard are polypeptides having the amino acid sequence of HUVCT36, variants, analogs, derivatives and fragments thereof, and variants, analogs and derivatives of the fragments which retain the activity/function of HUVCT36.

Among preferred variants are those that vary from a reference by conservative amino acid substitutions. Such substitutions are those that substitute a given amino acid in a polypeptide by another amino acid of like characteristics. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe and Tyr.

Further particularly preferred in this regard are variants, analogs, derivatives and fragments, and variants, analogs and derivatives of the fragments, having the amino acid sequence of the HUVCT36 polypeptide of FIG. 1, in which several, a few, 5 to 10, 1 to 5, 1 to 3, 2, 1 or no amino acid residues are substituted, deleted or added, in any combination. Especially preferred among these are silent substitutions, additions and deletions, which do not alter the properties and activities of the HUVCT36. Also especially preferred in this regard are conservative substitutions. Most highly preferred are polypeptides having the amino acid sequence of FIGS. 1A, 1B and 1C without substitutions.

The polypeptides and polynucleotides of the present invention are preferably provided in an isolated form, and preferably are purified to homogeneity.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention. Fragments may be "free-standing," i.e., not part of or fused to other amino acids or polypeptides, or they may be comprised within a larger polypeptide of which they form a part or region. When comprised within a larger polypeptide, the presently discussed fragments most preferably form a single continuous region. However, several fragments may be comprised within a single larger polypeptide. For instance, certain preferred embodiments relate to a fragment of a HUVCT36 polypeptide of the present comprised within a precursor polypeptide designed for expression in a host and having heterologous pre and pro-polypeptide regions fused to the amino terminus of the HUVCT36 fragment and an additional region fused to the carboxyl terminus of the fragment. Therefore, fragments in one aspect of the meaning intended herein, refers to the portion or portions of a fusion polypeptide or fusion protein derived from HUVCT36.

As representative examples of polypeptide fragments of the invention, there may be mentioned those which have from about 5–15, 10–20, 15–40, 30–55, 41–75, 41–80, 41–90, 50–100, 75–100, 90–115, 100–125, and 110–113 amino acids long.

In this context "about" includes the particularly recited range and ranges larger or smaller by several, a few, 5, 4, 3, 2 or 1 amino acid residues at either extreme or at both extremes. For instance, about 40–90 amino acids in this context means a polypeptide fragment of 40 plus or minus several, a few, 5, 4, 3, 2 or 1 amino acid residues to 90 plus or minus several a few, 5, 4, 3, 2 or 1 amino acid residues, i.e., ranges as broad as 40 minus several amino acids to 90 plus several amino acids to as narrow as 40 plus several amino acids to 90 minus several amino acids.

Highly preferred in this regard are the recited ranges plus or minus as many as 5 amino acids at either or at both extremes. Particularly highly preferred are the recited ranges plus or minus as many as 3 amino acids at either or at both the recited extremes. Especially particularly highly preferred are ranges plus or minus 1 amino acid at either or at both extremes or the recited ranges with no additions or deletions. Most highly preferred of all in this regard are fragments from about 5–15, 10–20, 15–40, 30–55, 41–75, 41–80, 41–90, 50–100, 75–100, 90–115, 100–125, and 110–113 amino acids long.

Also preferred in this aspect of the invention are fragments characterized by structural or functional attributes of HUVCT36. Preferred embodiments of the invention in this regard include fragments that comprise alpha-helix and alpha-helix forming regions ("alpha-regions"), beta-sheet and beta-sheet-forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, flexible regions, surface-forming regions and high antigenic index regions of HUVCT36.

Among highly preferred fragments in this regard are those that comprise regions of HUVCT36 that combine several structural features, such as several of the features set out above. In this regard, the regions defined by the residues about 10 to about 20, about 40 to about 50, about 70 to about 90 and about 100 to about 113 of FIGS. 1A, 1B and 1C, which all are characterized by amino acid compositions highly characteristic of turn-regions, hydrophilic regions, flexible-regions, surface-forming regions, and high antigenic index-regions, are especially highly preferred regions. Such regions may be comprised within a larger polypeptide or may be by themselves a preferred fragment of the present invention, as discussed above. It will be appreciated that the term "about" as used in this paragraph has the meaning set out above regarding fragments in general.

Further preferred regions are those that mediate activities of HUVCT36. Most highly preferred in this regard are fragments that have a chemical, biological or other activity of HUVCT36, including those with a similar activity or an improved activity, or with a decreased undesirable activity. Highly preferred in this regard are fragments that contain regions that are homologs in sequence, or in position, or in both sequence and to active regions of related polypeptides, such as platelet activating factor receptor, angiotensin type 2 receptor and purinoceptor. Among particularly preferred fragments are those comprising cytoplasmic, transmembrane and extracellular domains.

Among the fragments of the present invention include deletion of the transmembrane region only and retention of at least part of the cytoplasmic domain itself or fusion with at least part of an alternate cytoplasmic domain as described in WO96/04382.

It will be appreciated that the invention also relates to, among others, polynucleotides encoding the aforementioned fragments, polynucleotides that hybridize to polynucleotides encoding the fragments, particularly those that hybridize under stringent conditions, and polynucleotides, such as PCR primers, for amplifying polynucleotides that encode the fragments. In these regards, preferred polynucleotides are those that correspond to the preferred fragments, as discussed above.

Vectors, Host Cells, Expression

The present invention also relates to vectors which include polynucleotides of the present invention, host cells which are genetically engineered with vectors of the invention and the production of polypeptides of the invention by recombinant techniques.

Host cells can be genetically engineered to incorporate polynucleotides and express polypeptides of the present invention. For instance, polynucleotides may be introduced into host cells using well known techniques of infection, transduction, transfection, transvection and transformation. The polynucleotides may be introduced alone or with other polynucleotides. Such other polynucleotides may be introduced independently, cointroduced or introduced joined to the polynucleotides of the invention.

Thus, for instance, polynucleotides of the invention may be transfected into host cells with another, separate, polynucleotide encoding a selectable marker, using standard techniques for co-transfection and selection in, for instance, mammalian cells. In this case the polynucleotides generally will be stably incorporated into the host cell genome.

Alternatively, the polynucleotides may be joined to a vector containing a selectable marker for propagation in a host. The vector construct may be introduced into host cells by the aforementioned techniques. Generally, a plasmid vector is introduced as DNA in a precipitate, such as a calcium phosphate precipitate, or in a complex with a charged lipid. Electroporation may also be used to introduce polynucleotides into a host. If the vector is a virus, it may be packaged in vitro or introduced into a packaging cell and the packaged virus may be transduced into cells. A wide variety of techniques suitable for making polynucleotides and for introducing polynucleotides into cells in accordance with this aspect of the invention are well known and routine to those of skill in the art. Such techniques are reviewed at length in Sambrook et al., which is illustrative of the many laboratory manuals that detail these techniques.

In accordance with this aspect of the invention, the vector may be, for example, a plasmid vector, a single- or double-stranded phage vector, or a single- or double-stranded RNA or DNA viral vector. Such vectors may be introduced into cells as polynucleotides, preferably DNA, by well known techniques for introducing DNA and RNA into cells. The vectors, in the case of phage and viral vectors may also be, and preferably are, introduced into cells as packaged or encapsidated virus by well known techniques for infection and transduction. Viral vectors may be replication competent or replication defective. In the latter case, viral propagation generally will occur only in complementing host cells.

Preferred among vectors, in certain respects, are those for expression of polynucleotides and polypeptides of the present invention. Generally, such vectors comprise cis-acting control regions effective for expression in a host operatively linked to the polynucleotide to be expressed. Appropriate trans-acting factors either are supplied by the host, supplied by a complementing vector or supplied by the vector itself upon introduction into the host.

In certain preferred embodiments in this regard, the vectors provide for specific expression. Such specific expression may be inducible expression or expression only in certain types of cells or both inducible and cell-specific. Particularly preferred among inducible vectors are vectors that can be induced for expression by environmental factors that are easy to manipulate, such as temperature and nutrient additives. A variety of vectors suitable to this aspect of the invention, including constitutive and inducible expression vectors for use in prokaryotic and eukaryotic hosts, are well known and employed routinely by those of skill in the art.

The engineered host cells can be cultured in conventional nutrient media, which may be modified as appropriate for, inter alia, activating promoters, selecting transformants or amplifying genes. Culture conditions, such as temperature, pH and the like, previously used with the host cell selected for expression, generally will be suitable for expression of polypeptides of the present invention as will be apparent to those of skill in the art.

A great variety of expression vectors can be used to express a polypeptide of the invention. Such vectors include chromosomal, episomal and virus-derived vectors e.g., vectors derived from bacterial plasmids, from bacteriophage, from yeast episomes, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. Generally, any vector suitable to maintain, propagate or express polynucleotides to express a polypeptide in a host may be used for expression in this regard.

The appropriate DNA sequence may be inserted into the vector by any of a variety of well-known and routine techniques. In general, a DNA sequence for expression is joined to an expression vector by cleaving the DNA sequence and the expression vector with one or more restriction endonucleases and then joining the restriction fragments together using T4 DNA ligase. Procedures for restriction and ligation that can be used to this end are well known and routine to those of skill. Suitable procedures in this regard, and for constructing expression vectors using alternative techniques, which also are well known and routine to those skilled in the art, are set forth in great detail in Sambrook et al.

The DNA sequence in the expression vector is operatively linked to appropriate expression control sequence(s), including, for instance, a promoter to direct mRNA transcription. Representatives of such promoters include the phage lambda PL promoter, the *E. coli* lac, trp and tac promoters, the SV40 early and late promoters and promoters of retroviral LTRs, to name just a few of the well-known promoters. It will be understood that numerous other useful promoters in this aspect of the invention are well known and may be employed routinely by those of skill in the manner illustrated by the discussion and the examples herein.

In general, expression constructs will contain sites for transcription initiation and termination, and, in the transcribed region, a ribosome binding site for translation. The coding portion of the mature transcripts expressed by the constructs will include a translation initiating AUG at the beginning and a termination codon appropriately positioned at the end of the polypeptide to be translated.

In addition, the constructs may contain control regions that regulate as well as engender expression. Generally, in accordance with many commonly practiced procedures, such regions will operate by controlling transcription, such as repressor binding sites and enhancers, among others.

Vectors for propagation and expression generally will include selectable markers. Such markers also may be suitable for amplification or the vectors may contain additional markers for this purpose. In this regard, the expression vectors preferably contain one or more selectable marker genes to provide a phenotypic trait for selection of transformed host cells. Preferred markers include dihydrofolate reductase or neomycin resistance for eukaryotic cell culture, and tetracycline or ampicillin resistance genes for culturing *E. coli* and other bacteria.

The vector containing the appropriate DNA sequence as described elsewhere herein, as well as an appropriate promoter, and other appropriate control sequences, may be introduced into an appropriate host using a variety of well known techniques suitable for expression therein of a desired polypeptide. Representative examples of appropriate hosts include bacterial cells, such as *E. coli*, Streptomyces and *Salmonella typhimurium* cells; fungal cells, such as yeast cells; insect cells such as Drosophila S2 and Spodoptera Sf9 cells; animal cells such as CHO, COS and Bowes melanoma cells; and plant cells. Hosts of a great variety of expression constructs are well known, and those of skill will be enabled by the present disclosure to routinely select a host for expressing a polypeptide in accordance with this aspect of the present invention.

More particularly, the present invention also includes recombinant constructs, such as expression constructs, comprising one or more of the sequences described above. The constructs comprise a vector, such as a plasmid or viral vector, into which such a sequence of the invention has been inserted. The sequence may be inserted in a forward or reverse orientation. In certain preferred embodiments in this regard, the construct further comprises regulatory sequences, including, for example, a promoter, operably linked to the sequence. Large numbers of suitable vectors and promoters are known to those of skill in the art, and there are many commercially available vectors suitable for use in the present invention.

The following vectors, which are commercially available, are provided by way of example. Among vectors preferred for use in bacteria are pQE70, pQE60 and pQE-9, available from Qiagen; pBS vectors, Phagescript vectors, Bluescript vectors, pNH8A, pNH16a, pNH18A, pNH46A, available from Stratagene; ptrc99a, pKK223-3, pKK233-3, pDR540, pRIT5 available from Pharmacia, and pCDN, a SmithKline proprietary vector. Among preferred eukaryotic vectors are pWLNEO, pSV2CAT, pOG44, pXT1 and pSG available from Stratagene; pSVK3, pBPV, pMSG and pSVL available from Pharmacia; and pCDN. These vectors are listed solely by way of illustration of the many commercially available and well known vectors that are available to those of skill in the art for use in accordance with this aspect of the present invention. It will be appreciated that any other plasmid or vector suitable for, for example, introduction, maintenance, propagation or expression of a polynucleotide or polypeptide of the invention in a host may be used in this aspect of the invention.

Promoter regions can be selected from any desired gene using vectors that contain a reporter transcription unit lacking a promoter region, such as a chloramphenicol acetyl transferase ("CAT") transcription unit, downstream of a restriction site or sites for introducing a candidate promoter fragment; i.e., a fragment that may contain a promoter. As is well known, introduction into the vector of a promoter-containing fragment at the restriction site upstream of the CAT gene engenders production of CAT activity, which can be detected by standard CAT assays. Vectors suitable to this end are well known and readily available. Two examples of such vectors include pKK232-8 and pCM7. Thus, promoters for expression of polynucleotides of the present invention include not only well known and readily available promoters, but also promoters that may be readily obtained by the foregoing technique, using a reporter gene.

Among known bacterial promoters suitable for expression of polynucleotides and polypeptides in accordance with the present invention are the E. coli lacI and lacZ promoters, the T3 and T7 promoters, the gpt promoter, the lambda PR, PL promoters and the trp promoter.

Among known eukaiyotic promoters suitable in this regard are the CMV immediate early promoter, the HSV thymidine kinase promoter, the early and late SV40 promoters, the promoters of retroviral LTRs, such as those of the Rous sarcoma virus ("RSV"), and metallothionein promoters, such as the mouse metallothionein-I promoter.

Selection of appropriate vectors and promoters for expression in a host cell is a well known procedure and the requisite techniques for construction of expression vectors, introduction of the vector into the host and expression in the host are routine skills in the art.

The present invention also relates to host cells containing the above-described constructs discussed above. The host cell can be a higher eukaryotic cell, such as a mammalian cell, or a lower eukaryotic cell, such as a yeast cell, or a prokaryotic cell, such as a bacterial cell.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals.

Constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook et al.

Generally, recombinant expression vectors will include origins of replication, a promoter derived from a highly-expressed gene to direct transcription of a downstream structural sequence, and a selectable marker to permit isolation of vector containing cells following exposure to the vector. Among suitable promoters are those derived from the genes that encode glycolytic enzymes such as 3-phosphoglycerate kinase ("PGK"), a-factor, acid phosphatase, and heat shock proteins, among others. Selectable markers include the ampicillin resistance gene of E. coli and the trp 1 gene of S. cerevisiae.

Transcription DNA encoding the polypeptides of the present invention by higher eukaryotes may be increased by inserting an enhancer sequence into the vector. Enhancers are cis-acting elements of DNA, usually from about 10 to 300 bp that act to increase transcriptional activity of a promoter in a given host cell-type. Examples of enhancers include the SV40 enhancer, which is located on the late side of the replication origin at bp 100 to 270, the cytomegalovirus early promoter enhancer, the polyoma enhancer on the late side of the replication origin, and adenovirus enhancers.

A polynucleotide of the invention encoding the heterologous structural sequence of a polypeptide of the invention generally will be inserted into the vector using standard techniques so that it is operably linked to the promoter for expression. The polynucleotide will be positioned so that the transcription start site is located appropriately 5' to a ribosome binding site. The ribosome binding site will be 5' to the AUG that initiates translation of the polypeptide to be expressed. Generally, there will be no other open reading frames that begin with an initiation codon, usually AUG, and lie between the ribosome binding site and the initiating AUG. Also, generally, there will be a translation stop codon at the end of the polypeptide and there will be a polyadenylation signal and a transcription termination signal appropriately disposed at the 3' end of the transcribed region.

Appropriate secretion signals may be incorporated into the expressed polypeptide for secretion of the translated protein into the lumen of the endoplasmic reticulum, the periplasmic space or the extracellular environment. The signals may be endogenous to the polypeptide or may be heterologous.

The polypeptide may be expressed in a modified form, such as a fusion protein, and may include not only secretion signals but also additional heterologous functional regions. Thus, for instance, a region of additional amino acids, particularly charged amino acids, may be added to the N-terminus of the polypeptide to improve stability and persistence in the host cell, during purification or during subsequent handling and storage. A region may also be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art.

Suitable prokaryotic hosts for propagation, maintenance or expression of polynucleotides and polypeptides in accordance with the invention include *Escherichia coli, Bacillus subtilis* and *Salmonella typhimuriuinz*. Various species of Pseudomonas, Streptomyces, and Staphylococcus are also suitable hosts in this regard. Moreover, many other hosts also known to those of skill may be employed in this regard.

As a representative but non-limiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation, the host strain is grown to an appropriate cell density. Where the selected promoter is inducible, it is induced by appropriate means (e.g., temperature shift or exposure to chemical inducer) and cells are cultured for an additional period.

Cells typically then are harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well known to those skilled in the art.

Various mammalian cell culture systems can be employed for expression, as well. Examples of mammalian expression systems include the COS-7 line of monkey kidney fibroblasts, described in Gluzman et al., *Cell*, 1981, 23:175. Other cell lines capable of expressing a compatible vector include for example, the C127, 3T3, CHO, HeLa, human kidney 293 and BHK cell lines.

Mammalian expression vectors will comprise an origin of replication, a suitable promoter and enhancer, any necessary ribosome binding sites, polyadenylation sites, splice donor and acceptor sites, transcriptional termination sequences, and 5' flanking non-transcribed sequences that are necessary for expression. In certain preferred embodiments, DNA sequences derived from the SV40 splice sites, and the SV40 polyadenylation sites are used for required non-transcribed genetic elements of these types.

The HUVCT36 polypeptide can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Well known techniques for refolding proteins may be employed to regenerate active conformation when the polypeptide is denatured during isolation and or purification.

Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may include an initial modified methionine residue, in some cases as a result of host-mediated processes.

HUVCT36 polynucleotides and polypeptides may be used in accordance with the present invention for a variety of applications, particularly those that make use of the chemical and biological properties of HUVCT36. Additional applications relate to diagnosis and to treatment of disorders of cells, tissues and organisms. These aspects of the invention are illustrated further by the following discussion.

Polynucleotide Assays

This invention is also related to the use of HUVCT36 polynucleotides to detect complementary polynucleotides such as, for example, as a diagnostic reagent. Detection of a mutated form of HUVCT36 associated with a dysfunction will provide a diagnostic tool that can add to or define a diagnosis of a disease or susceptibility to a disease which results from under-expression, over-expression or altered expression of HUVCT36. Individuals carrying mutations in the human HUVCT36 gene may be detected at the DNA level by a variety of techniques. Nucleic acids for diagnosis may be obtained from a patient's cells, such as from blood, urine, saliva, tissue biopsy or autopsy material. The genomic DNA may be used directly for detection or may be amplified enzymatically by using PCR prior to analysis. (Saiki et al., *Nature*, 1986, 324:163–166). RNA or cDNA may also be used in similar fashion. As an example, PCR primers complementary to the nucleic acid encoding HUVCT36 can be used to identify and analyze HUVCT36 expression and mutations. For example, deletions and insertions can be detected by a change in size of the amplified product in comparison to the normal genotype. Point mutations can be identified by hybridizing amplified DNA to radiolabeled HUVCT36 RNA or alternatively, radiolabeled HUVCT36 antisense DNA sequences. Perfectly matched sequences can be distinguished from mismatched duplexes by RNase A digestion or by differences in melting temperatures.

Sequence differences between a reference gene and genes having mutations may also be revealed by direct DNA sequencing. In addition, cloned DNA segments may be employed as probes to detect specific DNA segments. The sensitivity of such methods can be greatly enhanced by appropriate use of PCR or another amplification method. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic testing based on DNA sequence differences may be achieved by detection of alteration in electrophoretic mobility of DNA fragments in gels, with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., *Science*, 1985, 230:1242).

Sequence changes at specific locations also may be revealed by nuclease protection assays, such as RNase and S1 protection or the chemical cleavage method (e.g., Cotton et al., *Proc. Natl. Acad. Sci., USA*, 1985, 85:4397–4401).

Thus, the detection of a specific DNA sequence may be achieved by methods such as hybridization, RNase protection, chemical cleavage, direct DNA sequencing or the use of restriction enzymes, (e.g., restriction fragment length polymorphisms ("RFLP") and Southern blotting of genomic DNA.

In accordance with a further aspect of the invention, there is provided a process for diagnosing or determining a susceptibility to migraine; infections, such as bacterial, fungal, protozoan and viral infections, particularly infection caused by HIV-1 or HIV-2; pain; cancers; anorexia; bulimia; asthma; Parkinson's disease; acute heart failure; hypotension; hypertension; urinary retention; osteoporosis; angina pectoris; myocardial infarction; ulcers; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome, among others. A mutation in the HUVCT36 gene indicates a susceptibility to infections, such as bacterial, fungal, protozoan and viral infections, particulaily infection caused by HIV-1 or HIV-2; pain; cancers; anorexia; bulimia; asthma; Parkinson's disease; acute heart failure; hypotension; hypertension; urinary retention; osteoporosis; angina pectoris; myocardial infarction; ulcers; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome, among others; and the nucleic acid sequences described above may be employed in an assay for ascertaining such susceptibility. Thus the assay may be employed, for example, to determine a mutation in a human HUVCT36 gene as herein described, such as a deletion, truncation, insertion, frame shift, etc., with such mutation being indicative of a susceptibility to infections, such as bacterial, fungal, protozoan and viral infections, particularly infection caused by HIV-1 or HIV-2; pain; cancers; anorexia; bulimia; asthma; Parkinson's disease; acute heart failure; hypotension; hypertension; urinary retention; osteoporosis; angina pectoris; myocardial infarction; ulcers; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome, among others.

The invention provides a process for diagnosing diseases, particularly infections, such as bacterial, fungal, protozoan and viral infections, more particularly infection caused by HIV-1 or HIV-2; pain; cancers; anorexia; bulimia; asthma; Parkinson's disease; acute heart failure; hypotension; hypertension; urinary retention; osteoporosis; angina pectoris; myocardial infarction; ulcers; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome, among others; comprising determining from a sample derived from a patient an abnormally decreased or increased level of expression of polynucleotide having the sequence of FIGS. 1A, 1B and 1C (SEQ ID NO:1). Decreased or increased expression of polynucleotide can be measured using any of the methods well known in the art for the quantitation of polynucleotides, such as, for example, PCR, RT-PCR, RNase protection, Northern blotting and other hybridization methods.

In addition to more conventional gel-electrophoresis and DNA sequencing, mutations can also be detected by in situ analysis.

Chromosome Assays

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with gene associated disease.

Briefly, sequences can be mapped to chromosomes by preparing PCR primers (preferably 15–25 bp) from the cDNA. Computer analysis of the 3' untranslated region is used to rapidly select primers that do not span more than one exon in the genomic DNA, because primers that span more than one exon can complicate the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNAs as short as 50 to 60 bases. For a review of this technique, see Verma et al., Human Chromosomes: A Manual of Basic Techniques, Pergamon Press, New York (1988).

As an example of how this technique is performed, HUVCT36 DNA is digested and purified with QIAEX II DNA purification kit (QIAGEN, Inc., Chatsworth, Calif.) and ligated to Super Cos1 cosmid vector (Stratagene, La Jolla, Calif.). DNA is purified using Qiagen Plasmid Purification Kit (Qiagen Inc., Chatsworth, Calif.) and 1 mg is labeled by nick translation in the presence of Biotin-dATP using BioNick Labeling Kit (GibcoBRL, Life Technologies Inc., Gaithersburg, Md.). Biotinylation is detected with GENE-TECT Detection System (Clontech Laboratories, Inc. Palo Alto, Calif.). In situ hybridization is performed on slides using ONCOR Light Hybridization Kit (Oncor, Gaithersberg, Md.) to detect single copy sequences on metaphase chromosomes. Peripheral blood of normal donors is cultured for three days in RPMI 1640 supplemented with 20% FCS, 3% PHA and penicillin/streptomycin, synchronized with $10^{-7}$ M methotrexate for 17 hours and washed twice with unsupplemented RPMI. Cells are then incubated with $10^{-3}$ M thymidine for 7 hours. The cells are arrested in metaphase after a 20 minute incubation with colcemid (0.5 μg/ml) followed by hypotonic lysis in 75 mM KCI for 15 minutes at 37° C. Cell pellets are then spun out and fixed in Carnoy's fixative (3:1 methanol/acetic acid).

Metaphase spreads are prepared by adding a drop of the suspension onto slides and air drying the suspension.

Hybridization is performed by adding 100 ng of probe suspended in 10 ml of hybridization mix (50% formainide, 2×SSC, 1% dextran sulfate) with blocking human placental DNA (1 μg/ml). Probe mixture is denatured for 10 minutes in a 70° C. water bath and incubated for 1 hour at 37° C., before placement on a prewarmed (37° C.) slide, and previously denatured in 70% formamide/2×SSC at 70° C., dehydrated in ethanol series and chilled to 4° C.

Slides are incubated for 16 hours at 37° C. in a humidified chamber. Slides are washed in 50% formamide/2×SSC for 10 minutes at 41° C. and 2×SSC for 7 minutes at 37° C. Hybridization probe is detected by incubation of the slides with FITC-Avidin (Oncor, Gaithersberg, Md.), according to the manufacturer's protocol. Chromosomes are counterstained with propridium iodine suspended in mounting medium. Slides are visualized using a Leitz ORTHOPLAN 2-epifluorescence microscope and five computer images are taken using a Imagenetics Computer and MacIntosh printer.

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

It is then necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes assuming 1 megabase mapping resolution and one gene per 20 kb.

Polypeptide Assays

The present invention also relates to diagnostic assays such as quantitative and diagnostic assays for detecting levels of HUVCT36 protein in cells and tissues, including determination of normal and abnormal levels. Thus, for instance, a diagnostic assay in accordance with the invention for detecting over-expression of HUVCT36 protein compared to normal control tissue samples may be used to detect the presence of a disease/disorder such as a bacterial, fungal, protozoan or viral infection, particularly infection caused by HIV1 or HIV-2; pain; cancers; anorexia; bulimia; asthma; Parkinson's disease; acute heart failure; hypotension; hypertension; urinary retention; osteoporosis; angina pectoris; myocardial infarction; ulcers; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome, among others. Assay techniques that can be used to determine levels of a protein, such as an HUVCT36 protein of the present invention, in a sample derived from a host are well-known to those of skill in the art. Such assay methods include radioimmunoassays, competitive-binding assays, Western Blot analysis and enzyme linked immunosorbent assays (ELISAs). Among these, ELISAs are frequently preferred. An ELISA assay initially comprises preparing an antibody specific to HUVCT36, preferably a monoclonal antibody. In addition a reporter antibody generally is prepared which binds to the monoclonal antibody. The reporter antibody is attached to a detectable reagent such as a radioactive, fluorescent or enzymatic reagent, in this example, horseradish peroxidase enzyme.

To carry out an ELISA, a sample is removed from a host and incubated on a solid support, e.g. a polystyrene dish, that binds the proteins in the sample. Any free protein binding sites on the dish are then covered by incubating with a non-specific protein such as bovine serum albumin. Next, the monoclonal antibody is incubated in the dish during which time the monoclonal antibodies attach to any HUVCT36 proteins attached to the polystyrene dish. Unbound monoclonal antibody is washed out with buffer. The reporter antibody linked to horseradish peroxidase is placed in the dish resulting in binding of the reporter antibody to any monoclonal antibody bound to HUVCT36. Unattached reporter antibody is then washed out. Reagents for peroxidase activity, including a colorimetric substrate, are then added to the dish. Immobilized peroxidase, linked to HUVCT36 through the primary and secondary antibodies, produces a colored reaction product. The amount of color developed in a given time period indicates the amount of HUVCT36 protein present in the sample. Quantitative results typically are obtained by reference to a standard curve.

A competition assay may also be employed wherein antibodies specific to HUVCT36 attached to a solid support and labeled HUVCT36 and a sample derived from the host are passed over the solid support. The amount of detected label attached to the solid support can be correlated to a quantity of HUVCT36 in the sample.

Antibodies

The polypeptides, their fragments or other derivatives, or analogs thereof, or cells expressing them can also be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptide itself. In this manner, even a sequence encoding only a fragment of a polypeptide can be used to generate antibodies binding the whole native polypeptide. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler, G. and Milstein, C., Nature, 1975, 256:495–497), the trioma technique, the human B-cell hybridoma technique (Kozbor et al., Immunology Today, 1983, 4:72) and the EBV-hybridoma technique to produce human monoclonal antibodies (Cole et al., pg. 77–96 in MONOCLONAL ANTIBODIES AND CANCER THERAPY, Alan R. Liss, Inc. (1985)).

Techniques described for the production of single chain antibodies (U.S. Pat. No. 4,946,778) can be adapted to produce single chain antibodies to immunogenic polypeptide products of this invention. Also, transgenic mice, or other organisms including other mammals, may be used to express humanized antibodies to immunogenic polypeptide products of this invention.

The above-described antibodies may be employed to isolate or to identify clones expressing the polypeptide or purify the polypeptide of the present invention by attachment of the antibody to a solid support for isolation and/or purification by affinity chromatography.

Antibodies against HUVCT36 can also be employed to inhibit infections, such as bacterial, fungal, protozoan and viral infections, particularly infection caused by HIV-1 or HIV-2; pain; cancers; anorexia; bulimia; asthma; Parkinson's disease; acute heart failure; hypotension; hypertension; urinary retention; osteoporosis; angina pectoris; myocardial infarction; ulcers; allergies; benign prostatic hypertrophy, and psychotic and neurological disorders, including anxiety, schizophrenia, manic depression, delirium, dementia, severe mental retardation and dyskinesias, such as Huntington's disease or Gilles dela Tourett's syndrome, among others.

HUVCT36 Binding Molecules and Assays

HUVCT36 can be used to isolate proteins which interact with it; this interaction can be a target for interference. Inhibitors of protein-protein interactions between HUVCT36 and other factors could lead to the development of pharmaceutical agents for the modulation of HUVCT36 activity.

Thus, this invention also provides a method for identification of binding molecules to HUVCT36. Genes encoding proteins for binding molecules to HUVCT36 can be identified by numerous methods known to those of skill in the art, for example, ligand panning and FACS sorting. Such methods are described in many laboratory manuals such as, for instance, Coligan et al., Current Protocols in Immunology 1: Chapter 5 (1991).

The HUVCT36 receptor can be expressed in a mammalian, lower eukaryotic and/or yeast cells and used to screen complex biological mixtures, compound banks, and combinatorial peptide and/or organic libraries for natural and surrogate ligands which are agonists and/or antagonists. Screening assays employed include radiolabeled binding assays and/or functional assays including, but not limited to, calcium mobilization, chemotaxis, cAMP accumulation, adenylyl cyclase turnover, GTPγ binding, phospholipase C turnover, and inositol 1,4,5-triphosphate ($IP_3$) and diacylglycerol turnover. The mnicrophysiometer and frog melanocyte systems may also be used for functional screens.

For example, the yeast two-hybrid system provides methods for detecting the interaction between a first test protein and a second test protein, in vivo, using reconstitution of the activity of a transcriptional activator. The method is disclosed in U.S. Pat. No. 5,283,173; reagents are available from Clontech and Stratagene. Briefly, HUVCT36 cDNA is fused to a Gal4 transcription factor DNA binding domain and expressed in yeast cells. cDNA library members obtained from cells of interest are fused to a transactivation domain of Gal4. cDNA clones which express proteins which can interact with HUVCT36 will lead to reconstitution of Gal4 activity and transactivation of expression of a reporter gene such as Gal1-lacZ.

An alternative method is screening of λgt11, λZAP (Stratagene) or equivalent cDNA expression libraries with recombinant HUVCT36. Recombinant HUVCT36 protein or fragments thereof are fused to small peptide tags such as FLAG, HSV or GST. The peptide tags can possess convenient phosphorylation sites for a kinase such as heart muscle creatine kinase or they can be biotinylated. Recombinant HUVCT36 can be phosphorylated with $^{32}[P]$ or used unlabeled and detected with streptavidin or antibodies against the tags. λgt11cDNA expression libraries are made from cells of interest and are incubated with the recombinant HUVCT36, washed and cDNA clones which interact with HUVCT36 isolated. Such methods are routinely used by skilled artisans. See, e.g., Sambrook et al.

Another method is the screening of a mammalian expression library. In this method cDNAs are cloned into a vector between a mammalian promoter and polyadenylation site and transiently transfected in COS or 293 cells. Forty-eight hours later the binding protein is detected by incubation of fixed and washed cells with a labeled HUVCT36. In preferred embodiments, the HUVCT36 is iodinated, and detection of any bound HUVCT36 is detected via autoradiography. See Sims et al., *Science*, 1988, 241:585–589 and McMahan et al., *EMBO J.*, 1991, 10:2821–2832. In this manner, pools of cDNAs containing the cDNA encoding the binding protein of interest can be selected and the cDNA of interest can be isolated by further subdivision of each pool followed by cycles of transient transfection, binding and autoradiography. Alternatively, the cDNA of interest can be isolated by transfecting the entire cDNA library into mammalian cells and panning the cells on a dish containing HUVCT36 bound to the plate. Cells which attach after washing are lysed and the plasmid DNA isolated, amplified in bacteria, and the cycle of transfection and panning repeated until a single cDNA clone is obtained. See Seed et al, *Proc. Natl. Acad. Sci. USA*, 1987, 84:3365 and Aruffo et al., *EMBO J.*, 1987, 6:3313. If the binding protein is secreted, its cDNA can be obtained by a similar pooling strategy once a binding or neutralizing assay has been established for assaying supernatants from transiently transfected cells. General methods for screening supernatants are disclosed in Wong et al., *Science*, 1985, 228:810–815.

Another alternative method is isolation of proteins interacting with HUVCT36 directly from cells. Fusion proteins of HUVCT36 with GST or small peptide tags are made and immobilized on beads. Biosynthetically labeled or unlabeled protein extracts from the cells of interest are prepared, incubated with the beads and washed with buffer. Proteins interacting with HUVCT36 are eluted specifically from the beads and analyzed by SDS-PAGE. Binding partner primary amino acid sequence data are obtained by microsequencing. Optionally, the cells can be treated with agents that induce a functional response such as tyrosine phosphorylation of cellular proteins. An example of such an agent would be a growth factor or cytokine such as interleukin-2.

Another alternative method is inimunoaffinity purification. Recombinant HUVCT36 is incubated with labeled or unlabeled cell extracts and immunoprecipitated with anti-HUVCT36 antibodies. The immunoprecipitate is recovered with protein A-Sepharose and analyzed by SDS-PAGE. Unlabelled proteins are labeled by biotinylation and detected on SDS gels with streptavidin. Binding partner proteins are analyzed by microsequencing. Further, standard biochemical purification steps known to those skilled in the art may be used prior to microsequencing.

Yet another alternative method is screening of peptide libraries for binding partners. Recombinant tagged or labeled HUVCT36 is used to select peptides from a peptide or phosphopeptide library which interact with HUVCT36. Sequencing of the peptides leads to identification of consensus peptide sequences which might be found in interacting proteins.

HUVCT36 binding partners identified by any of these methods or other methods which would be known to those of ordinary skill in the art, as well as those putative binding partners discussed above, can be used in the assay method of the invention. Assaying for the presence of HUVCT36/ binding partner complex is accomplished by, for example, the yeast two-hybrid system, ELISA or immunoassays using antibodies specific for the complex. In the presence of test substances which interrupt or inhibit formation of HUVCT36/binding partner interaction, a decreased amount of complex will be determined relative to a control lacking the test substance.

Assays for free HUVCT36 or binding partner are accomplished by, for example, ELISA or immunoassay using specific antibodies or by incubation of radiolabeled HUVCT36 with cells or cell membranes followed by centrifugation or filter separation steps. In the presence of test substances which interrupt or inhibit formation of HUVCT36/binding partner interaction, an increased amount of free HUVCT36 or free binding partner is determined relative to a control lacking the test substance.

Polypeptides of the invention can also be used to assess HUVCT36 binding capacity of HUVCT36 binding molecules in cells or in cell-free preparations.

Agonists and Antagonists—Assays and Molecules

HUVCT36 of the present invention may be employed in a process for screening for compounds which activate (agonists) or inhibit activation (antagonists) of the receptor polypeptide of the present invention.

In general, such screening procedures involve providing appropriate cells which express the receptor polypeptide of the present invention on the surface thereof. Such cells include cells from mammals, yeast, Drosophila or E. coli. In particular, a polynucleotide encoding the receptor of the present invention is employed to transfect cells to thereby express the HUVCT36. The expressed receptor is then contacted with a test compound to observe binding, stimulation or inhibition of a functional response. Test compounds may be, for example, complex biological mixtures, combinatorial peptide and/or organic libraries, organic compounds, peptides, tissues or cell extracts.

One such screening procedure involves the use of melanophores which are transfected to express the HUVCT36 of the present invention. Such a screening technique is described in PCT WO92/01810 published Feb. 6, 1992.

Such an assay may be employed to screen for a compound which inhibits activation of the receptor polypeptide of the present invention by contacting the melanophore cells which encode the receptor with both the receptor ligand and a compound to be screened. Inhibition of the signal generated by the ligand indicates that a compound is a potential antagonist for the receptor, i.e., inhibits activation of the receptor.

The technique may also be employed for screening of compounds which activate the receptor by contacting such cells with compounds to be screened and determining whether such compound generates a signal, i.e., activates the receptor.

Other screening techniques include the use of cells which express the HUVCT36 (for example, transfected CHO cells) in a system which measures extracellular pH or intracellular calcium changes caused by receptor activation. In this technique, compounds may be contacted with cells expressing the receptor polypeptide of the present invention. A second messenger response, e.g., signal transduction, pH changes, or an increase in calcium, is then measured to determine whether the potential compound activates or inhibits the receptor.

Another such screening technique involves introducing RNA encoding the HUVCT36 into Xenopus oocytes to transiently express the receptor. The receptor oocytes are then contacted with the receptor ligand and a compound to be screened. Inhibition or activation of the receptor is then determined by detection of a signal, such as, calcium, proton, or other ions.

Another screening technique involves expressing the HUVCT36 linked to phospholipase C or D. Representative examples of such cells, include, but are not limited to, endothelial cells, smooth muscle cells and embryonic kidney cells. The screening is accomplished as hereinabove described by detecting activation of the receptor or inhibition of activation of the receptor from the phospholipase second signal.

Another method involves screening for compounds which are antagonists, and thus inhibit activation of the receptor polypeptide of the present invention, by determining inhibition of binding of labeled ligand to cells which have the receptor on the surface thereof. Such a method involves transfecting a eukaryotic cell with DNA encoding the HUVCT36 such that the cell expresses the receptor on its surface. The cell is then contacted with a compound in the presence of a labeled form of a known ligand. The ligand can be labeled, e.g., by radioactivity. The amount of labeled ligand bound to the receptors is measured, e.g., by measuring radioactivity associated with transfected cells or membrane from these cells. If the compound binds to the receptor, the binding of labeled ligand to the receptor is inhibited as determined by a reduction of labeled ligand which binds to the receptors.

Another method involves screening for HUVCT36 inhibitors by determining inhibition or stimulation of HUVCT36-mediated cAMP and/or adenylate cyclase accumulation. Such a method involves transfecting a eukaryotic cell with HUVCT36 receptor to express the receptor on the cell surface. The cell is then exposed to potential antagonists in the presence of HUVCT36. The amount of cAMP accumulation is then measured. If the potential antagonist binds the receptor, and thus inhibits HUVCT36 binding, the levels of HUVCT36-mediated cAMP, or adenylate cyclase, activity will be reduced or increased.

Another methods for detecting agonists or antagonists for the receptor of the present invention is the yeast based technology as described in U.S. Pat. No. 5,482,835.

The present invention also provides a method for determining whether a ligand not known to be capable of binding to a HUVCT36 receptor can bind to such receptor which comprises contacting a mammalian cell which expresses a HUVCT36 receptor with the ligand under conditions permitting binding of ligands to the HUVCT36 receptor, and detecting the presence of a ligand which binds to the receptor thereby determining whether the ligand binds to the HUVCT36 receptor. The systems hereinabove described for determining agonists and/or antagonists may also be employed for determining ligands which bind to the receptor.

Examples of potential HUVCT36 receptor antagonists include antibodies or, in some cases, oligonucleotides, which bind to the receptor but do not elicit a second messenger response such that the activity of the receptor is prevented.

Potential antagonists also include proteins which are closely related to the ligand of the HUVCT36 receptor, i.e. a fragment of the ligand, which has lost biological function and, when binding to the HUVCT36 receptor, elicits no response.

A potential antagonist also includes antisense construct prepared through the use of antisense technology. Antisense technology can be used to control gene expression through triple-helix formation or antisense DNA or RNA, both methods of which are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix -see Lee et al., Nucl. Acids Res., 1979, 6:3073; Cooney et al, Science, 1988, 241:456 and Dervan et al., Science, 1991, 251:1360), thereby preventing transcription and production of the HUVCT36 receptor. The antisense RNA oligonucleotide hybridizes to the mRNA in vivo and blocks translation of the MRNA molecule to the HUVCT36 receptor (antisense—Okano, J. Neurochem., 1991, 56:560; Oligodeoxynucleotides as Antisense Inhibitors of Gene Expression, CRC Press, Boca Raton, Fla. (1988)). The oligonucleotides described above can also be delivered to cells such that the antisense RNA or DNA is expressed in vivo to inhibit production of the HUVCT36 receptor.

Another potential antagonist is a small molecule which binds to the HUVCT36 receptor, making it inaccessible to ligands such that normal biological activity is prevented. Examples of small molecules include, but are not limited to, small peptides or peptide-like molecules.

Potential antagonists also include soluble forms of HUVCT36 receptors, e.g. fragments of the receptor, which bind to the ligand and prevent the ligand from interacting with membrane bound HUVCT36 receptors.

HUVCT36 proteins are ubiquitous in the mammalian host and are responsible for many biological functions, including many pathologies. Accordingly, it is desirous to find compounds and drugs which stimulate HUVCT36 on the one hand and which can inhibit the function of HUVCT36 on the other hand.

In general, agonists for a HUVCT36 receptor are employed for therapeutic and prophylactic purposes for such diseases or disorders as infections, such as bacterial, fungal, protozoan and viral infections, particularly infection caused by HIV-1 or HIV-2; pain; cancers; anorexia; bulimia; asthma; Parkinson's disease; acute heart failure; hypotension; hypertension; urinary retention; osteoporosis; angina pectoris; myocardial infarction; ulcers; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome among others.

Antagonists for HUVCT36 may be employed for a variety of therapeutic and prophylactic purposes for such diseases or disorders including infections, such as bacterial, fungal, protozoan and viral infections, particularly infection caused by HIV-1 or HIV-2; pain; cancers; anorexia; bulimia; asthma; Parkinson's disease; acute heart failure; hypotension; hypertension; urinary retention; osteoporosis; angina pectoris; myocardial infarction; ulcers; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome, among others.

This invention additionally provides a method of treating an abnormal condition related to an excess of HUVCT36 activity which comprises administering to a subject the inhibitor compounds (antagonists) as hereinabove described along with a pharmaceutically acceptable carrier in an amount effective to inhibit activation by blocking binding of ligands to the HUVCT36 receptor, or by inhibiting a second signal, and thereby alleviating the abnormal conditions.

The invention also provides a method of treating abnormal conditions related to an under-expression of HUVCT36 activity which comprises administering to a subject a therapeutically effective amount of a compound which activates the receptor polypeptide of the present invention (agonists) as described above in combination with a pharmaceutically acceptable carrier, to thereby alleviate the abnormal conditions.

Compositions and Kits

The soluble form of the HUVCT36, and compounds which activate or inhibit such receptor, may be employed in combination with a suitable pharmaceutical carrier. Such compositions comprise a therapeutically effective amount of the polypeptide or compound, and a pharmaceutically acceptable carrier or excipient. Such a carrier includes but is not limited to saline, buffered saline, dextrose, water, glycerol, ethanol, and combinations thereof. The formulation should suit the mode of administration.

The invention further relates to pharmaceutical packs and kits comprising one or more containers filled with one or more of the ingredients of the aforementioned compositions of the invention.

Administration

Polypeptides and other compounds of the present invention may be employed alone or in conjunction with other compounds, such as therapeutic compounds.

The pharmaceutical compositions may be administered in any effective, convenient manner including, for instance, administration by topical, oral, anal, vaginal, intravenous, intraperitoneal, intramuscular, subcutaneous, intrrinasal or intraidermal routes, among others.

The pharmaceutical compositions generally are administered in an amount effective for treatment or prophylaxis of a specific indication or indications. In general, the compositions are administered in an amount of at least about 10 $\mu$g/kg body weight. In most cases they will be administered in an amount not in excess of about 8 mg/kg body weight per day. Preferably, in most cases, the dose administered is from about 10 $\mu$g/kg to about 1 mg/kg body weight, daily. It will be appreciated that optimum dosage will be determined by standard methods for each treatment modality and indication, taking into account the indication, its severity, route of administration, complicating conditions and the like.

Gene Therapy

The HUVCT36 polynucleotides, polypeptides, agonists and antagonists that are polypeptides may be employed in accordance with the present invention by expression of such polypeptides in vivo, in treatment modalities often referred to as "gene therapy."

Thus, for example, cells from a patient may be engineered with a polynucleotide, such as a DNA or RNA, to encode a polypeptide ex vivo. The engineered cells can then be provided to a patient to be treated with the polypeptide. In this embodiment, cells may be engineered ex vivo, for example, by the use of a retroviral plasmid vector containing RNA encoding a polypeptide of the present invention. Such methods are well-known in the art and their use in the present invention will be apparent from the teachings herein.

Similarly, cells may be engineered in vivo for expression of a polypeptide in vivo by procedures known in the art. For example, a polynucleotide of the invention may be engineered for expression in a replication defective retroviral vector, as discussed above. The retroviral expression construct may then be isolated and introduced into a packaging cell transduced with a retroviral plasmid vector containing RNA encoding a polypeptide of the present invention such that the packaging cell now produces infectious viral particles containing the gene of interest. These producer cells may be administered to a patient for engineering cells in vivo and expression of the polypeptide in vivo. These and other methods for administering a polypeptide of the present invention should be apparent to those skilled in the art from the teachings of the present invention.

Retroviruses from which the retroviral plasmid vectors herein above mentioned may be derived include, but are not limited to, Moloney Murine Leukemia Virus, Spleen Necrosis Virus, Rous Sarcoma Virus, Harvey Sarcoma Virus, Avian Leukosis Virus, Gibbon Ape Leukemia Virus, Human Immunodeficiency Virus, Adenovirus, Myeloproliferative Sarcoma Virus, and Mammary Tumor Virus. In one preferred embodiment, the retroviral plasmid vector is derived from Moloney Murine Leukemia Virus.

Such vectors will include one or more promoters for expressing the polypeptide. Suitable promoters which may be employed include, but are not limited to, the retroviral LTR; the SV40 promoter; and the human cytomegalovirus (CMV) promoter described in Miller et al., *Biotechniques*, 1989, 7:980–990 or any other promoter (e.g., cellular promoters such as eukaryotic cellular promoters including, but not limited to, the histone, RNA polymerase III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention will be placed under the control of a suitable promoter. Suitable promoters which may be employed include, but are not limited to, adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs herein above described); the β-actin promoter; and human growth hormone promoters. The promoter may also be the native promoter which controls the gene encoding the polypeptide.

The retroviral plasmid vector is employed to transduce packaging cell lines to form producer cell lines. Examples of packaging cells which may be transfected include, but are not limited to, the PE501, PA317, Y-2, Y-AM, PA12, T19-14X, VT-19-17-H2, YCRE, YCRIP, GP+E-86, GP+envAm12, and DAN cell lines as described in Miller, A., *Human Gene Therapy*, 1990, 1:5–14. The vector may be transduced into the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line will generate infectious retroviral vector particles, which include the nucleic acid sequence(s) encoding the polypeptides. Such retroviral vector particles may then be employed to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial to cells.

EXAMPLES

The present invention is further described by the following examples. The examples are provided solely to illustrate the invention by reference to specific embodiments. These exemplification's, while illustrating certain specific aspects of the invention, do not portray the limitations or circumscribe the scope of the disclosed invention.

Certain terms used herein are explained in the foregoing glossary.

All examples are carried out using standard techniques, which are well known and routine to those of skill in the art, except where otherwise described in detail. Routine molecular biology techniques of the following examples can be carried out as described in standard laboratory manuals, such as Sambrook et al.

Example 1

Mammalian Cell Expression

The receptors of the present invention are expressed in either human embryonic kidney 293 (HEK293) cells or adherent dhfr CHO cells. To maximize receptor expression, all 5' and 3' untranslated regions (UTRs) are removed from the receptor cDNA prior to insertion into a CDN or pCDNA3 vector. The cells are transfected with individual receptor cDNAs by lipofectin and selected in the present of 400 µg/ml G418. After 3 weeks of selection, individual clones are picked and expanded for further analysis. HEK293 or CHO cells transfected with the vector alone serve as negative controls. To isolate cell lines stably expressing the individual orphan receptors, about 24 clones are typically selected and analyzed by Northern blot analysis. Receptor mRNAs a generally detectably in about 50% of the G418-resistant clones analyzed.

Example 2

Ligand Binding Assays

Ligand binding assays provide a direct method for ascertaining receptor function and are adaptable to a high throughput format. A bank of over 200 putative orphan receptor ligands has been assembled for initial screening. The bank comprises: transmitters, hormones and chemokines known to act via a human seven transmembrane (7TM) receptor; naturally occurring compounds which may be putative agonists for a human 7TM receptor, non-mammalian, biologically active peptides for which a mammalian counter part has not yet been identified; and compounds not found in nature, but which activate 7TM receptors with unknown natural ligands. This bank is used to initially screen the receptor for known ligands. The minimal dissociation constant of a ligand for its receptor in order to configure a reliable radioligand binding assay is about 10 nM.

The purified ligand for an orphan receptor is radiolabeled to high specific activity (50–1000 Ci/mmol) for binding studies. A determination is then made that the process of radiolabeling does not diminish the activity of the ligand towards its receptor. Assay conditions for buffers, ions, pH and other modulators such as nucleotides are optimized to establish a workable signal to noise ratio for both membrane and whole cell receptor sources. For these assays, specific receptor binding is defined as total associated radioactivity minus the radioactivity measured in the presence of an excess of unlabeled competing ligand. Where possible, more than one competing ligand is used to define residual non-specific binding. About 50% specific binding is considered optimal.

The relevance of the radioligand binding site as a receptor is defined by the following criteria. These criteria are derived from the definition of a receptor as a moiety that specifically recognizes the appropriate agonist and antagonist ligands through binding interactions and initiates a defined biological response. The criteria include: (1) the kinetics of radioligand binding approximating the kinetics of the agent's effect on the biological response; (2) the specific binding of increasing concentrations of radioligand becomes saturated thus reflecting a finite receptor population; (3) the concentration range over which the radioligand binds parallels the concentration range over which the ligand activates or inhibits a biological response; and (4) the receptor sites occupied by the radioligand demonstrate the appropriate pharmacological specificity as the biological response.

Example 3

Functional Assay in Xenopus Oocytes

Capped RNA transcripts from linearized plasmid templates encoding the orphan receptor cDNAs of the invention are synthesized in vitro with RNA polymerases in accordance with standard procedures. In vitro transcripts are suspended in water at a final concentration of 0.2 $\mu g/\mu l$. Ovarian lobes are removed from adult female toads, Stage V defolliculated oocytes are obtained, and RNA transcripts (10 ng/oocyte) are injected in a 50 nl bolus using a Drummond microinjection apparatus. Two electrode voltage clamps are used to measure the currents from individual Xenopus oocytes. Recordings are made in $Ca^{2+}$free Barth's medium at room temperature.

Example 4

Microphysiometric Assays

Activation of a wide variety of secondary messenger systems results in extrusion of small amounts of acid from a cell. The acid formed is largely as a result of the increased metabolic activity required to fuel the intracellular signaling process. The pH changes in the media surrounding the cell are very small but are detectable by the CYTOSENSOR microphysiometer (Molecular Devices Ltd., Menlo Park, Calif.). The CYTOSENSOR is thus capable of detecting the activation of a receptor which is coupled to an energy utilizing intracellular signaling pathway such as the G-protein coupled receptor of the present invention.

Example 5

Extract/Cell Supernatant Screening

A large number of mammalian peptides exist for which there remains, as yet, no mammalian equivalent. Thus, active ligands for this receptor may not be included within the ligands banks as identified to date. Accordingly, the orphan TM receptor of the invention is also screened against tissue extracts to identify natural ligands.

Example 6

Calcium Functional Assay

7TM receptors which are expressed in HEK 293 cells have been shown to be coupled functionally to activation of PLC and calcium mobilization. Basal calcium levels in the HEK 293 cells in receptor-transfected or vector control cells were observed to be in the normal, 100 nm to 200 nm, range. HEK 293 cells expressing recombinant receptors are loaded with fura 2 and in a single day >150 selected ligands are evaluated for agonist induced calcium mobilization. Agonists presenting a calcium transient are tested in vector control cells to determine if the response is unique to the transfected receptor cells. When a unique agonist-induced response is identified, the response will be reproduced in a separate group of cells and then pharmacologically characterized with concentration response curves for the effective and related ligands.

SEQUENCE LISTING (1) GENERAL INFORMATION:

(iii) NUMBER OF SEQUENCES:  3

(2) INFORMATION FOR SEQ ID NO:1:

(i) SEQUENCE CHARACTERISTICS:
      (A) LENGTH: 1597
      (B) TYPE:  Nucleic Acid
      (C) STRANDEDNESS:  Single
      (D) TOPOLOGY:  Linear (iv) ANTI-SENSE:  No (xi) SEQUENCE DESCRIPTION:  SEQ ID NO: 1:

```
GAGCTCGAGC GATCCCCACC TCCCAAAGTG CTGGGCTTAC AGGTGTAAGC           50

CATCATGTCC AGCCGTTCAG ATATTCTAGT TGAATTGGAG TTGGTGGGCT          100

AGTACACCTT CTAAATTAAA TGAGTAAAGG ATTTAGAATG GTGCCTGACA          150

CACAGTAGGT GCTACATTCA TGTTAGCTAC TATTATAAAC CTTTCCTGCC          200

TCTGACTTTC AGGGTCTTGC CCACCACCAG CGATGCCCAG CCCTTGGTAG          250

AGCTTGAACC ACCTTCTATA AACAGGATGG CGGTGGAGAG ACAGGCCCAG          300

TCCCTGAGCC CATGAGGAGT GTGGCCCCTT CAGGCCCAAA GATGGGGAAC          350

ATCACTGCAG ACAACTCCTC GATGAGCTGT ACCATCGACC ATACCATCCA          400
```

-continued

```
CCAGACGCTG GCCCCGGTGG TCTATGTTAC CGTGCTGGTG GTGGGCTTCC         450

CGGCCAACTG CCTGTCCCTC TACTTCGGCT ACCTGCAGAT CAAGGCCCGG         500

AACGAGCTGG GCGTGTACCT GTGCAACCTG ACGGTGGCCG ACCTCTTCTA         550

CATCTGCTCG CTGCCCTTCT GGCTGCAGTA CGTGCTGCAG CACGACAACT         600

GGTCTCACGG CGACCTGTCC TGCCAGGTGT GCGGCATCCT CCTGTACGAG         650

AACATCTACA TCAGCGTGGG CTTCCTCTGC TGCATCTCCG TGGACCGCTA         700

CCTGGCTGTG GCCCATCCCT TCCGCTTCCA CCAGTTCCGG ACCCTGAAGG         750

CGGCCGTCGG CGTCAGCGTG GTCATCTGGG CCAAGGAGCT GCTGACCAGC         800

ATCTACTTCC TGATGCACGA GGAGGTCATC GAGGACGAGA ACCAGCACCG         850

CGTGTGCTTT GAGCACTACC CCATCCAGGC ATGGCAGCGC GCCATCAACT         900

ACTACCGCTT CCTGGTGGGC TTCCTCTTCC CCATCTGCCT GCTGCTGGCG         950

TCCTACCAGG GCATCCTGCG CGCCGTGCGC CGGAGCCACG GCACCCAGAA        1000

GAGCCGCAAG GACCAGATCC AGCGGCTGGT GCTCAGCACC GTGGTCATCT        1050

TCCTGGCCTG CTTCCTGCCC TACCACGTGT TGCTGCTGGT GCGCAGCGTC        1100

TGGGAGGCCA GCTGCGACTT CGCCAAGGGC GTTTTCAACG CCTACCACTT        1150

CTCCCTCCTG CTCACCAGCT TCAACTGCGT CGCCGACCCC GTGCTCTACT        1200

GCTTCGTCAG CGAGACCACC CACCGGGACC TGGCCCGCCT CCGCGGGGCC        1250

TGCCTGGCCT TCCTCACCTG CTCCAGGACC GGCCGGGCCA GGGAGGCCTA        1300

CCCGCTGGGT GCCCCCGAGG CCTCCGGGAA AGCGGGGCC CAGGGTGAGG         1350

AGCCCGAGCT GTTGACCAAG CTCCACCCGG CCTTCCAGAC CCCTAACTCG        1400

CCAGGGTCGG GCGGGTTCCC CACGGGCAGG TTGGCCTAGC CTGGGTCCTC        1450

CGCGGGTGGC TCCACGTGAG GCCTGAGCCT TCAGCCCACG GGCCTCAGGG        1500

CCTGCCGCCT CCTGCTTCCC TCGCTGCGGA GGCAGGGAAG CCCCTGTAAC        1550

TCCGGAAGCC TGCTCTCGCT TGCTGAGCCC GCTGGGACCG CCGAGGT           1597
```

(2) INFORMATION FOR SEQ ID NO:2:

(i) SEQUENCE CHARACTERISTICS:
        (A) LENGTH: 531
        (B) TYPE: Amino Acid
        (D) TOPOLOGY: Linear (xi) SEQUENCE DESCRIPTION: SEQ ID NO: 2:

```
Ala Arg Ala Ile Pro Thr Ser Gln Ser Ala Gly Leu Thr Gly Val
1               5                  10                  15

Ser His His Val Gln Pro Phe Arg Tyr Ser Ser Xaa Ile Gly Val
                20                  25                  30

Gly Gly Leu Val His Leu Leu Asn Xaa Met Ser Lys Gly Phe Arg
                35                  40                  45

Met Val Pro Asp Thr Gln Xaa Val Leu His Ser Cys Xaa Leu Leu
                50                  55                  60

Leu Xaa Thr Phe Pro Ala Ser Asp Phe Gln Gly Leu Ala His His
                65                  70                  75

Gln Arg Cys Pro Ala Leu Gly Arg Ala Xaa Thr Thr Phe Tyr Lys
                80                  85                  90

Gln Asp Gly Gly Gly Glu Thr Gly Pro Val Pro Glu Pro Met Arg
                95                 100                 105

Ser Val Ala Pro Ser Gly Pro Lys Met Gly Asn Ile Thr Ala Asp
```

```
                        110                 115                 120
Asn Ser Ser Met Ser Cys Thr Ile Asp His Thr Ile His Gln Thr
                125                 130                 135
Leu Ala Pro Val Val Tyr Val Thr Val Leu Val Val Gly Phe Pro
                140                 145                 150
Ala Asn Cys Leu Ser Leu Tyr Phe Gly Tyr Leu Gln Ile Lys Ala
                155                 160                 165
Arg Asn Glu Leu Gly Val Tyr Leu Cys Asn Leu Thr Val Ala Asp
                170                 175                 180
Leu Phe Tyr Ile Cys Ser Leu Pro Phe Trp Leu Gln Tyr Val Leu
                185                 190                 195
Gln His Asp Asn Trp Ser His Gly Asp Leu Ser Cys Gln Val Cys
                200                 205                 210
Gly Ile Leu Leu Tyr Glu Asn Ile Tyr Ile Ser Val Gly Phe Leu
                215                 220                 225
Cys Cys Ile Ser Val Asp Arg Tyr Leu Ala Val Ala His Pro Phe
                230                 235                 240
Arg Phe His Gln Phe Arg Thr Leu Lys Ala Ala Val Gly Val Ser
                245                 250                 255
Val Val Ile Trp Ala Lys Glu Leu Leu Thr Ser Ile Tyr Phe Leu
                260                 265                 270
Met His Glu Glu Val Ile Glu Asp Glu Asn Gln His Arg Val Cys
                275                 280                 285
Phe Glu His Tyr Pro Ile Gln Ala Trp Gln Arg Ala Ile Asn Tyr
                290                 295                 300
Tyr Arg Phe Leu Val Gly Phe Leu Phe Pro Ile Cys Leu Leu Leu
                305                 310                 315
Ala Ser Tyr Gln Gly Ile Leu Arg Ala Val Arg Arg Ser His Gly
                320                 325                 330
Thr Gln Lys Ser Arg Lys Asp Gln Ile Gln Arg Leu Val Leu Ser
                335                 340                 345
Thr Val Val Ile Phe Leu Ala Cys Phe Leu Pro Tyr His Val Leu
                350                 355                 360
Leu Leu Val Arg Ser Val Trp Glu Ala Ser Cys Asp Phe Ala Lys
                365                 370                 375
Gly Val Phe Asn Ala Tyr His Phe Ser Leu Leu Leu Thr Ser Phe
                380                 385                 390
Asn Cys Val Ala Asp Pro Val Leu Tyr Cys Phe Val Ser Glu Thr
                395                 400                 405
Thr His Arg Asp Leu Ala Arg Leu Arg Gly Ala Cys Leu Ala Phe
                410                 415                 420
Leu Thr Cys Ser Arg Thr Gly Arg Ala Arg Glu Ala Tyr Pro Leu
                425                 430                 435
Gly Ala Pro Glu Ala Ser Gly Lys Ser Gly Ala Gln Gly Glu Glu
                440                 445                 450
Pro Glu Leu Leu Thr Lys Leu His Pro Ala Phe Gln Thr Pro Asn
                455                 460                 465
Ser Pro Gly Ser Gly Gly Phe Pro Thr Gly Arg Leu Ala Xaa Pro
                470                 475                 480
Gly Ser Ser Ala Gly Gly Ser Thr Xaa Gly Leu Ser Leu Gln Pro
                485                 490                 495
Thr Gly Leu Arg Ala Cys Arg Leu Leu Leu Pro Ser Leu Arg Arg
                500                 505                 510
```

```
Gln Gly Ser Pro Cys Asn Ser Gly Ser Leu Leu Ser Leu Ala Glu
            515                 520                 525

Pro Ala Gly Thr Ala Glu
            530

(2) INFORMATION FOR SEQ ID NO:3:

(i) SEQUENCE CHARACTERISTICS:
        (A) LENGTH: 365
        (B) TYPE: Amino Acid
        (D) TOPOLOGY: Linear (xi) SEQUENCE DESCRIPTION: SEQ ID NO: 3:

Met Gly Asn Ile Thr Ala Asp Asn Ser Ser Met Ser Cys Thr Ile
1                5                  10                  15

Asp His Thr Ile His Gln Thr Leu Ala Pro Val Val Tyr Val Thr
                20                  25                  30

Val Leu Val Val Gly Phe Pro Ala Asn Cys Leu Ser Leu Tyr Phe
                35                  40                  45

Gly Tyr Leu Gln Ile Lys Ala Arg Asn Glu Leu Gly Val Tyr Leu
                50                  55                  60

Cys Asn Leu Thr Val Ala Asp Leu Phe Tyr Ile Cys Ser Leu Pro
                65                  70                  75

Phe Trp Leu Gln Tyr Val Leu Gln His Asp Asn Trp Ser His Gly
                80                  85                  90

Asp Leu Ser Cys Gln Val Cys Gly Ile Leu Leu Tyr Glu Asn Ile
                95                  100                 105

Tyr Ile Ser Val Gly Phe Leu Cys Cys Ile Ser Val Asp Arg Tyr
                110                 115                 120

Leu Ala Val Ala His Pro Phe Arg Phe His Gln Phe Arg Thr Leu
                125                 130                 135

Lys Ala Ala Val Arg Val Thr Val Val Ile Trp Ala Lys Glu Leu
                140                 145                 150

Leu Thr Ser Ile Tyr Phe Leu Met His Glu Glu Val Ile Glu Asp
                155                 160                 165

Glu Asn Gln His Arg Val Cys Phe Glu His Tyr Pro Ile Gln Ala
                170                 175                 180

Trp Gln Arg Ala Ile Asn Tyr Tyr Arg Phe Leu Val Gly Phe Leu
                185                 190                 195

Phe Pro Ile Cys Leu Leu Leu Ala Ser Tyr Gln Gly Ile Leu Arg
                200                 205                 210

Ala Val Arg Arg Ser His Gly Thr Gln Lys Ser Arg Lys Asp Gln
                215                 220                 225

Ile Gln Arg Leu Val Leu Ser Thr Val Val Ile Phe Leu Ala Cys
                230                 235                 240

Phe Leu Pro Tyr His Val Leu Leu Leu Val Arg Ser Val Trp Glu
                245                 250                 255

Ala Ser Cys Asp Phe Ala Lys Gly Val Phe Asn Ala Tyr His Phe
                260                 265                 270

Ser Leu Leu Leu Thr Ser Phe Asn Cys Val Ala Asp Pro Val Leu
                275                 280                 285

Tyr Cys Phe Val Ser Glu Thr Thr His Arg Asp Leu Ala Arg Leu
                290                 295                 300

Arg Gly Ala Cys Leu Ala Phe Leu Thr Cys Ser Arg Thr Gly Arg
                305                 310                 315

Ala Arg Glu Ala Tyr Pro Leu Gly Ala Pro Glu Ala Ser Gly Lys
```

-continued

```
                        320                 325                 330
Ser Gly Ala Gln Gly Glu Glu Pro Glu Leu Leu Thr Lys Leu His
                335                 340                 345
Pro Ala Phe Gln Thr Pro Asn Ser Pro Gly Ser Gly Gly Phe Pro
                350                 355                 360
Thr Gly Arg Leu Ala
                365
```

What is claimed is:

1. An isolated polynucleotide comprising a nucleotide sequence that has at least 95% identity to a polynoucleotide sequence encoding the amino acid sequence of SEQ ID NO:2 ; or a nucleotide sequence complementary to said polnucleotide sequence, wherein said identity is over the entire coding region for SEQ ID NO:2, and is calculated using FASTA wherein sequences are aligned so that the largest match between the two sequences is obtained.

2. The isolated polynucleotide of claim 1 which is DNA or RNA.

3. The isolated polynucleotide of claim 1 wherein said nucleotide sequence is at least 95% identical to that contained in SEQ ID NO:1, wherein said identity is over the entire length of SEQ ID NO:1, and is calculated using FASTA wherein sequences are aligned so that the largest match between the two sequences is obtained.

4. The isolated polynucleotide of claim 3 wherein said nucleotide sequence comprises nucleotides 1–1593 as set forth in SEQ ID NO:1.

5. The polynucleotide of claim 3 having the polynucleotide sequence of SEQ ID NO:1.

* * * * *

UNITED STATES PATENT AND TRADEMARK OFFICE
CERTIFICATE OF CORRECTION

Page 1 of 2

PATENT NO. : 5,912,335
DATED : June 15, 1999
INVENTOR(S) : Bergsma, et al.

It is certified that error appears in the above-identified patent and that said Letters Patent is hereby corrected as shown below:

Please insert the attached figure 2.

Signed and Sealed this

Eleventh Day of July, 2000

Attest:

Q. TODD DICKINSON

*Attesting Officer*          Director of Patents and Trademarks

UNITED STATES PATENT AND TRADEMARK OFFICE
CERTIFICATE OF CORRECTION

Page 2 of 2

PATENT NO. : 5,912,335
DATED : June 15, 1999
INVENTOR(S) : Bergsma, et al.

It is certified that error appears in the above-identified patent and that said Letters Patent is hereby corrected as shown below:

```
  1 MRSVAPSGPKMGNITADNSSMSCTIDHTIHQTLAPVVYVTVLVVGFPANC  50
             |||||||||||||||||||||||||||||||||||||||
  1 .........MGNITADNSSMSCTIDHTIHQTLAPVVYVTVLVVGFPANC  40

51 LSLYFGYLQIKARNELGVYLCNLTVADLFYICSLPFWLQYVLQHDNWSHG 100
    |||||||||||||||||||||||||||||||||||||||||||||||||
 41 LSLYFGYLQIKARNELGVYLCNLTVADLFYICSLPFWLQYVLQHDNWSHG  90

101 DLSCQVCGILLYENIYISVGFLCCISVDRYLAVAHPFRFHQFRTLKAAVG 150
    ||||||||||||||||||||||||||||||||||||||||||||||||
 91 DLSCQVCGILLYENIYISVGFLCCISVDRYLAVAHPFRFHQFRTLKAAVR 140

151 VSVVIWAKELLTSIYFLMHEEVIEDENQHRVCFEHYPIQAWQRAINYYRF 200
    |.|||||||||||||||||||||||||||||||||||||||||||||||
141 VTVVIWAKELLTSIYFLMHEEVIEDENQHRVCFEHYPIQAWQRAINYYRF 190

201 LVGFLFPICLLLASYQGILRAVRRSHGTQKSRKDQIQRLVLSTVVIFLAC 250
    |||||||||||||||||||||||||||||||||||||||||||||||||
191 LVGFLFPICLLLASYQGILRAVRRSHGTQKSRKDQIQRLVLSTVVIFLAC 240

251 FLPYHVLLLVRSVWEASCDFAKGVFNAYHFSLLLTSFNCVADPVLYCFVS 300
    |||||||||||||||||||||||||||||||||||||||||||||||||
241 FLPYHVLLLVRSVWEASCDFAKGVFNAYHFSLLLTSFNCVADPVLYCFVS 290

301 ETTHRDLARLRGACLAFLTCSRTGRAREAYPLGAPEASGKSGAQGEEPEL 350
    |||||||||||||||||||||||||||||||||||||||||||||||||
291 ETTHRDLARLRGACLAFLTCSRTGRAREAYPLGAPEASGKSGAQGEEPEL 340

351 LTKLHPAFQTPNSPGSGGFPTGRLA 375
    |||||||||||||||||||||||||
341 LTKLHPAFQTPNSPGSGGFPTGRLA 365
```